(12) United States Patent
Qu

(10) Patent No.: US 8,457,727 B2
(45) Date of Patent: Jun. 4, 2013

(54) MONITORING VARIATION PATTERNS IN PHYSIOLOGICAL PARAMETERS ASSOCIATED WITH MYOCARDIAL INSTABILITY

(75) Inventor: Fujian Qu, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1097 days.

(21) Appl. No.: 12/340,352

(22) Filed: Dec. 19, 2008

(65) Prior Publication Data
US 2010/0160804 A1 Jun. 24, 2010

(51) Int. Cl.
*A61N 1/362* (2006.01)

(52) U.S. Cl.
USPC ............................................. 600/516; 607/9

(58) Field of Classification Search
USPC .................. 600/508–509, 515–518; 607/17, 607/27, 122
See application file for complete search history.

(56) References Cited

U.S. PATENT DOCUMENTS

| 6,823,213 | B1 * | 11/2004 | Norris et al. .................... 607/9 |
| 7,171,258 | B2 | 1/2007 | Goode |
| 7,336,995 | B2 | 2/2008 | Armoundas et al. |
| 2004/0267142 | A1 | 12/2004 | Paul |
| 2005/0010122 | A1 | 1/2005 | Nearing et al. |
| 2007/0049835 | A1 | 3/2007 | Goode |
| 2009/0192398 | A1 * | 7/2009 | Zhou et al. .................... 600/517 |
| 2009/0318822 | A1 * | 12/2009 | Qu et al. ....................... 600/515 |

FOREIGN PATENT DOCUMENTS

WO    WO 2005/002435    1/2005

OTHER PUBLICATIONS

Online Real Time Detection of Atrial Fibrillation, Lu, Sheng et al, Department of Biomedical Engineering, Medicine (Cardiology), State University of New York, Stony Brook, Heart Rhythm 2007, 16 pgs.

* cited by examiner

*Primary Examiner* — Rex R Holmes
(74) *Attorney, Agent, or Firm* — Theresa Raymer; Steven M. Mitchell

(57) ABSTRACT

A method of analyzing myocardial instability includes obtaining a physiological parameter representative of myocardial behavior over a set of cardiac cycles and determining reversal points in the physiological parameter over the set of cardiac cycles. The method also includes identifying myocardial instability based on the reversal points in the physiological parameter. A reversal point may correspond to a value of the physiological parameter, during a current cardiac cycle, that exceeds or is less than the values of the physiological parameter during prior and subsequent cardiac cycles. Optionally, the method includes calculating differences between values of the physiological parameter for consecutive cardiac cycles and detecting the reversal points when a current difference exceeds or is less than differences for prior and subsequent cardiac cycles.

19 Claims, 10 Drawing Sheets

MONITORING VARIATION PATTERNS IN PHYSIOLOGICAL PARAMETERS ASSOCIATED WITH MYOCARDIAL INSTABILITY

FIELD OF THE INVENTION

Embodiments of the present invention pertain generally to implantable and external medical devices, and more particularly pertain to methods and systems that monitor myocardial instability.

BACKGROUND OF THE INVENTION

Sudden cardiac death (SCD) is the major cause of cardiac mortality and affects over 400,000 individuals per year in the United States. SCD often occurs in patients with coronary artery disease, cardiomyopathy, and ion channelopathies. SCD may be caused by a ventricular tachyarrhythmia that degenerates into ventricular fibrillation. Less commonly, bradyarrhythmias are associated as the initiating event of sudden cardiac death.

Many patients at risk of sudden cardiac death have pacemakers, implantable cardioverter defibrillators (ICDs) or other medical devices implanted therein. These devices may continuously obtain cardiac signals that are digitized and presented as electrocardiograms (ECG). ECGs are composed of various waves and segments that represent the heart depolarizing and repolarizing. The ST segment in an ECG represents the portion of the cardiac signal between ventricular depolarization and ventricular repolarization. While P-waves, R-waves, and T-waves in the ECG may generally be considered features of a surface ECG, for convenience and generality, herein the terms R-wave, T-wave, and P-wave are also used to refer to the corresponding internal cardiac signal, such as an intra-cardiac electrogram (IEGM) signal. Additionally, modern implant devices also may provide other types of cardiac related signals such as blood pressure and impedance in a continuous or periodical nature.

ECG, IEGM, pressure measurements, and impedance measurements may be useful for monitoring unstable myocardial behavior within the heart, which may lead to the onset of ventricular tachyarrhythmias in the future. Yet, in spite of the known risk stratification methods, accurate prediction of the onset of sudden cardiac death remains a relatively difficult and imperfect task. Additionally, the known implantable devices hardware may limit the usage of comprehensive algorithms that exceed device capability. Thus, a method and system are needed for implantable devices to track myocardial instability, predict the onset of sudden cardiac death, and/or deliver preventive therapy.

BRIEF SUMMARY OF THE INVENTION

In one embodiment, a method of analyzing myocardial instability is provided. The method includes obtaining a physiological parameter representative of myocardial behavior over a set of cardiac cycles and determining reversal points in the physiological parameter over the set of cardiac cycles. The method also includes identifying myocardial instability based on the reversal points in the physiological parameter. A reversal point may correspond to a value of the physiological parameter, during a current cardiac cycle, that exceeds or is less than the values of the physiological parameter during prior and subsequent cardiac cycles. Optionally, the method includes calculating differences between values of the physiological parameter for consecutive cardiac cycles and detecting the reversal points when a current difference exceeds or is less than differences for prior and subsequent cardiac cycles.

In another embodiment, a computer readable storage medium for a computing device having a memory and a microcontroller is provided. The computer readable storage medium includes instructions to direct the memory to store a physiological parameter representative of myocardial behavior over a set of cardiac cycles. The instructions direct the microcontroller to determine reversal points in the physiological parameter over the set of cardiac cycles and identify myocardial instability based on the reversal points in the physiological parameter. Optionally, the instructions may direct the microcontroller to determine the first and last reversal points in the set of cardiac cycles and identify myocardial instability based at least in part on a number of heartbeats between the first and last reversal points. The instructions may direct the microcontroller to calculate a reversal point percentage based on a relation of a number of the reversal points and a number of heartbeats between the first and last reversal points.

In another embodiment, a device for analyzing myocardial instability is provided. The device includes a memory and a microcontroller. The memory stores physiological parameters obtained by an implantable medical device and representative of myocardial behavior over a set of cardiac cycles. The microcontroller determines reversal points in the physiological parameter over the set of cardiac cycles and identifies myocardial instability based on the reversal points in the physiological parameter. Optionally, the microcontroller initiates a responsive action when myocardial instability is identified. The microcontroller may calculate a reversal point percentage for each of multiple sets of cardiac cycles and determine a trend in the reversal point percentages, where the reversal point percentage for each set of cardiac cycles being based on a number of the reversal points in the set.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

Figure 1:
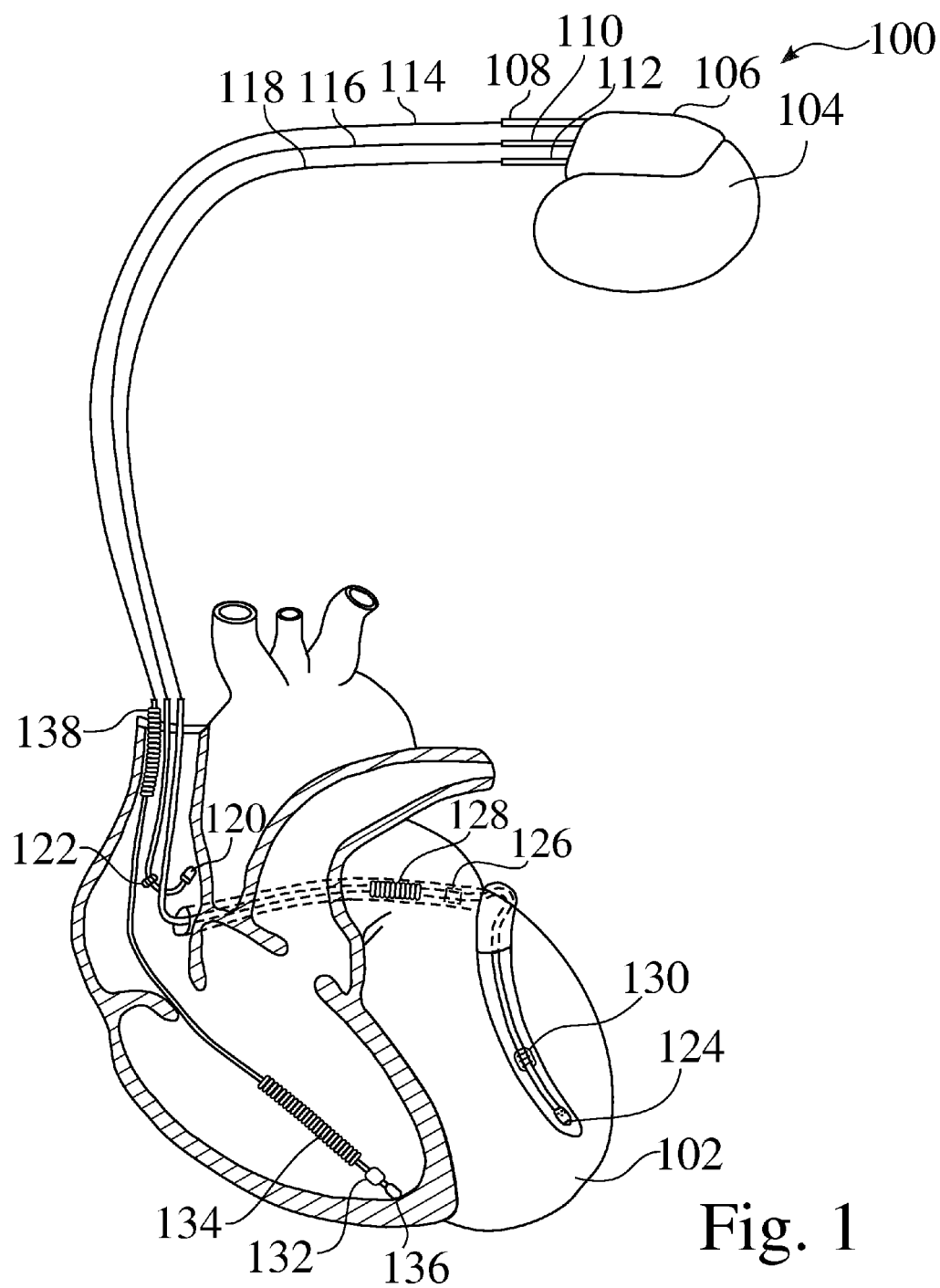
FIG. 1 illustrates an IMD that is coupled to a heart in a patient.

FIG. 1 illustrates an IMD 100 that is coupled to a heart 102 in a patient. The IMD 100 may be a cardiac pacemaker, an ICD, a defibrillator, an ICD coupled with a pacemaker, and the like, implemented in accordance with one embodiment of the present invention. The IMD 100 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. As explained below in more detail, the IMD 100 may be controlled to monitor physiological parameters that are used by an external device 828 (shown in FIG. 8) to monitor myocardial instability.

The IMD 100 includes a housing 104 that is joined to a header assembly 106 (e.g., an IS-4 connector assembly) that holds receptacle connectors 108, 110, 112 that are connected to a right ventricular lead 114, a right atrial lead 116, and a coronary sinus lead 118, respectively. The leads 114, 116, and 118 may be located at various locations, such as an atrium, a ventricle, or both to measure the physiological condition of the heart 102. To sense atrial cardiac signals and to provide right atrial chamber stimulation therapy, the right atrial lead 116 has at least an atrial tip electrode 120, which typically is implanted in the right atrial appendage, and an atrial ring electrode 122.

The coronary sinus lead 118 receives atrial and ventricular cardiac signals and delivers left ventricular pacing therapy using at least a left ventricular ("LV") tip electrode 124, delivers left atrial ("LA") pacing therapy using at least a left atrial ring electrode 126, and delivers shocking therapy using at least an LA coil electrode 128. The coronary sinus lead 118 also is connected with a LV ring electrode 130 disposed between the LV tip electrode 124 and the left atrial ring electrode 126. The right ventricular ("RV") lead 114 has an RV tip electrode 136, an RV ring electrode 132, an RV coil electrode 134, and an SVC coil electrode 138. The RV lead 114 is capable of receiving cardiac signals, and delivering stimulation in the form of pacing and shock therapy to the right ventricle.

The leads 114, 116, and 118 detect IEGM signals that form an electrical activity indicator of myocardial function over multiple cardiac cycles. The IEGM signals represent analog signals that are subsequently digitized and analyzed to identify waveforms or segment intervals of the IEGM signals. Examples of waveforms identified from the IEGM signals include the P-wave, T-wave, the R-wave, the QRS complex, the ST segment, and the like.

Figure 2:
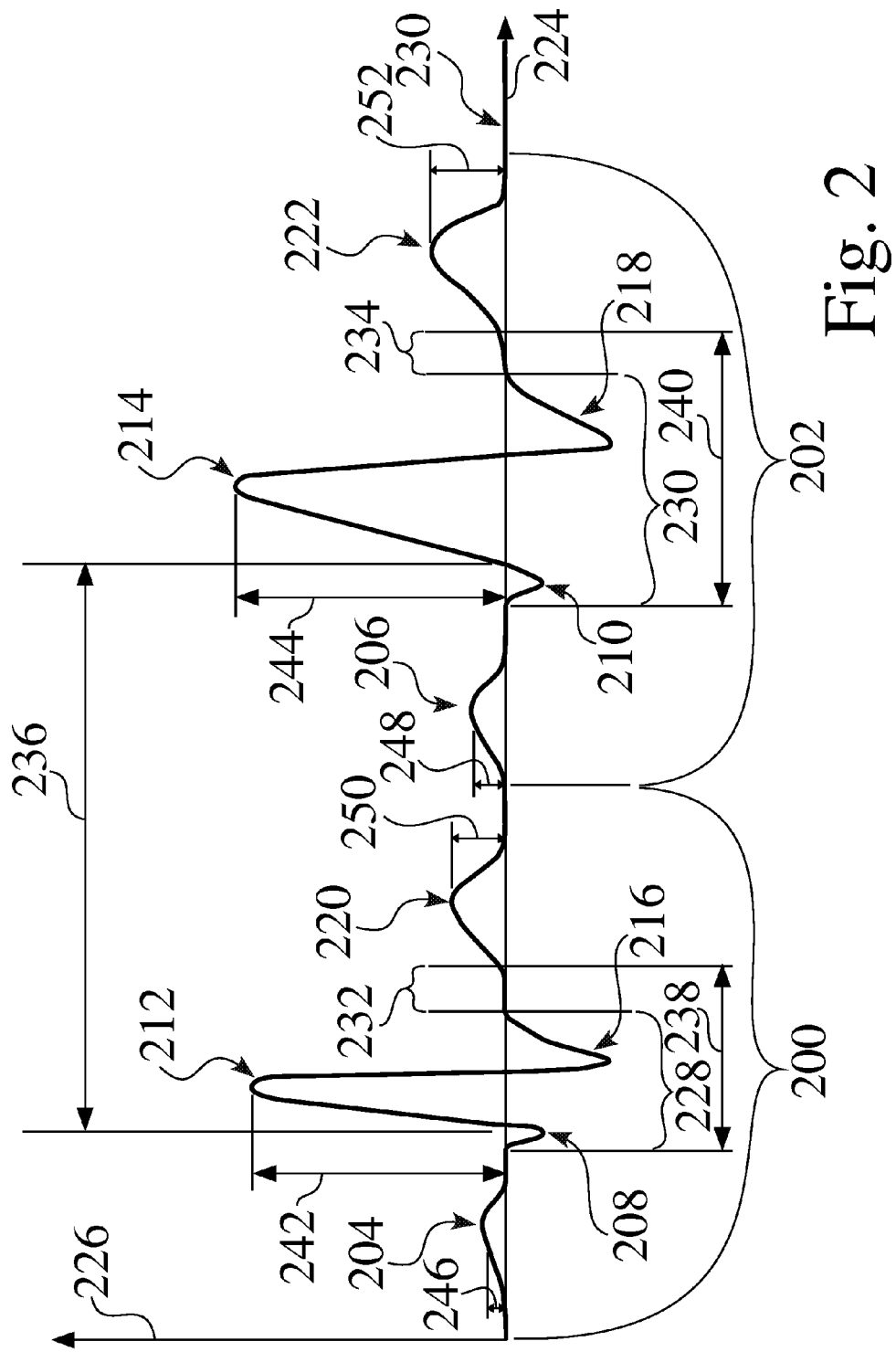
FIG. 2 illustrates two cardiac cycles that include P-waves, Q-waves, R-waves, S-waves, and T-waves.

FIG. 2 illustrates two cardiac cycles 200, 202 that include P-waves 204, 206, Q-waves 208, 210, R-waves 212, 214, S-waves 216, 218, and T-waves 220, 222. The cardiac cycles 200, 202 may represent cardiac signals, such as IEGM signals, ECG signals, cardiogenic impedance signals, and the like. The horizontal axis 224 represents time, while the vertical axis 226 is defined in units of voltage. A QRS complex 228, 230 in each cardiac cycle 200, 202 is composed of the Q-wave 208, 210, the R-wave 212, 214, and the S-wave 220, 222. The QRS complex 228, 230 is used to locate the R-wave 212, 214 to determine a baseline 230. The baseline 230 is shown as being coextensive with the horizontal axis 224 in the illustrated embodiment, although the baseline may be located above or below the horizontal axis 224. The portion of the signal in each cardiac cycle 200, 202 between the S-wave 216, 218 and T-wave 220, 222 constitutes an ST segment 232, 234.

The consecutive cardiac cycles 200, 202 include several intervals between waves. For example, the cardiac cycles 200, 202 include an R-R interval 236 that extends along the horizontal axis 224 between the R-waves 212, 214 in the cycles 200, 202. A Q-T interval 238, 240 in each cardiac cycle 200, 202 extends between the Q-wave 208, 210 and the T-wave 220, 222 in each cycle 200, 202. Other intervals may extend between waves within one cardiac cycle 200, 202 or between one wave in the first cardiac cycle 200 and a wave in the second cardiac cycle 202.

The distance that the waves and complexes in the cardiac cycles 200, 202 extend along the vertical axis 226 from the baseline 230 is the amplitude of the corresponding waves and complexes. For example, a QRS amplitude 242, 244 is the distance along the vertical axis 226 that the QRS complex 238, 240 extends above the baseline 230 in each cardiac cycle 200, 202. The P-wave amplitude 246, 248 is the distance along the vertical axis 226 that the P-wave 204, 206 extends above the baseline 230. The T-wave amplitude 250, 252 is the distance along the vertical axis 226 that the T-wave 220, 222 extends above the baseline 230. Although not shown in FIG. 2, the amplitude of other waves and complexes in the cardiac cycles 200, 202 may be measured.

In a heart 102 with stable myocardial behavior, the values of certain physiological parameters measured during multiple cardiac cycles 200, 202 remain approximately the same across a set of multiple cardiac cycles 200, 202. For example, the size of the R-R wave interval 236 between consecutive cardiac cycles 200, 202 may remain approximately the same for multiple cardiac cycles. In another example, the Q-T intervals 238, 240 or the amplitude of one or more waveforms do not significantly vary among multiple cardiac cycles 200, 202. In a heart 102 demonstrating instable myocardial behavior, the values of one or more physiological parameters may vary among the cardiac cycles 200, 202 in a set of the cardiac cycles. For example, the T-wave amplitude 250 may increase and decrease among multiple cardiac cycles 200, 202. The increasing and decreasing of the values of physiological parameters among multiple cardiac cycles 200, 202 in a set of cardiac cycles 200, 202 may indicate instability of the heart 102. Instability of the physiological parameters among multiple cardiac cycles 200, 202 may be an indication of impending sudden cardiac death. Therefore, monitoring variation patterns in physiological parameters related to the heart 102 may provide a more accurate manner for predicting the onset of sudden cardiac death.

Figure 3:
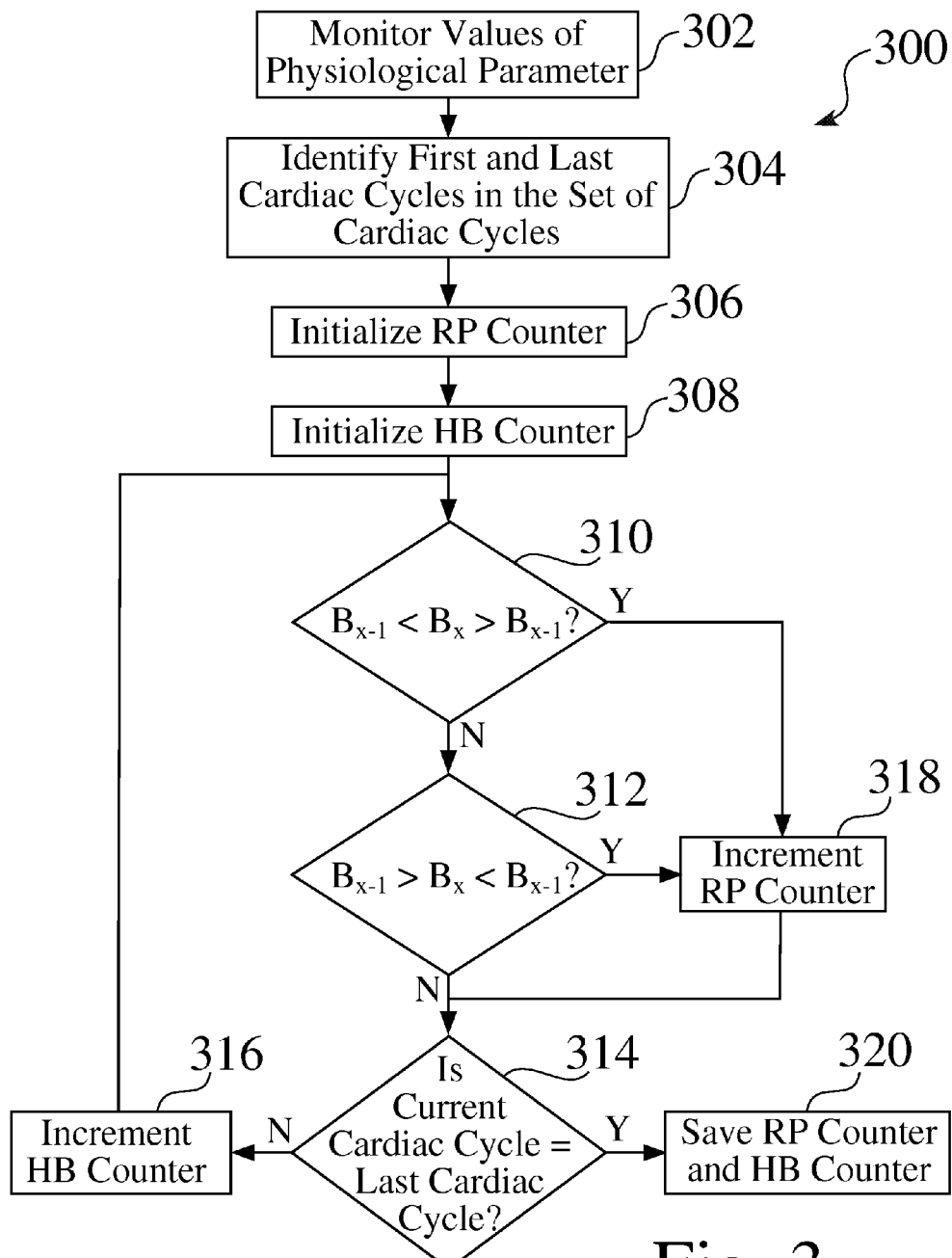
FIG. 3 illustrates a process for counting reversal points in values of a physiological parameter associated with a set of cardiac cycles.

FIG. 3 illustrates a process 300 for counting reversal points in the values of a physiological parameter associated with a set of cardiac cycles. The process 300 may be performed in whole or part by a variety of devices and systems including the IMD 100 (shown in FIG. 1) and devices communicatively coupled with the IMD 100. For example, the actions described below in connection with the process 300 may be performed by the IMD 100 and a device external to the IMD 100. The external device may include a programmer 828 (shown in FIG. 8) and/or an operator workstation 1010 (shown in FIG. 10), for example.

The values of one or more physiological parameters related to the heart 102 are monitored over a set of cardiac cycles at 302. For example, the length or duration of the Q-T interval 238, 240 (shown in FIG. 2) may be measured for each cardiac cycle in a set of cardiac cycles 200, 202. In one embodiment, the set of cardiac cycles includes at least three consecutive cardiac cycles. The set of cardiac cycles may be based on the duration of a monitoring window. A monitoring window is a length of time that the values of the physiological parameters in the cardiac cycles are measured. By way of example only, the number of cardiac cycles in the set of cardiac cycles may include the number of cardiac cycles that occur within a monitoring window of 2 minutes.

Figure 4:
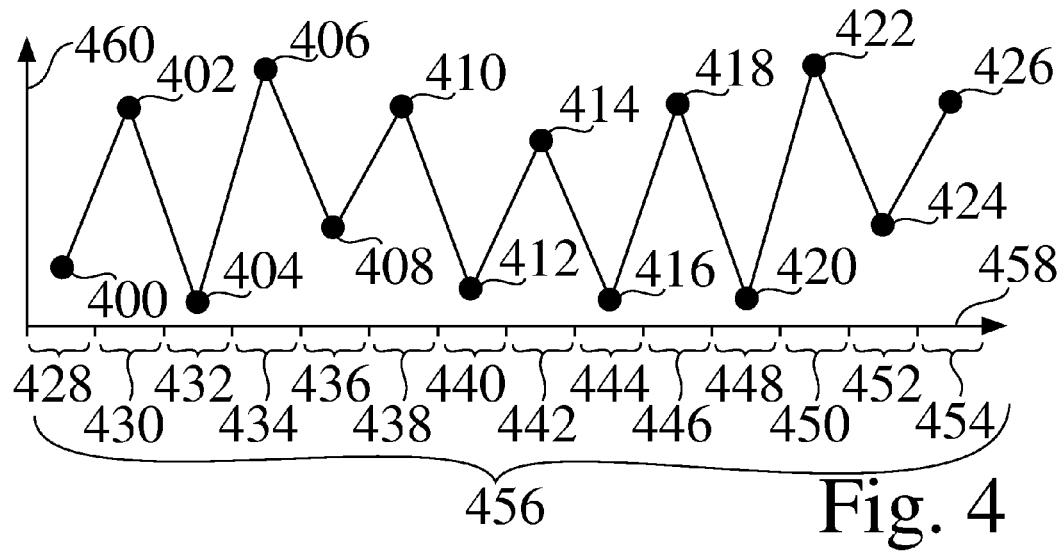
FIG. 4 is a graphic illustration of values of a physiological parameter that are measured during each cardiac cycle in a set of the cardiac cycles.

With continued reference to FIG. 3, FIG. 4 is a graphic illustration of values 400-426 of a physiological parameter that are measured during each cardiac cycle 428-454 in a set 456 of the cardiac cycles. The values 400-426 may be measured in whole or part by a variety of devices and systems. For example, the IMD 100 (shown in FIG. 1) may sense cardiac signals of the heart 102 (shown in FIG. 1) and determine the values 400-426. In another example, the IMD 100 may sense cardiac signals and communicate the cardiac signals to an external device to determine the values 400-426. As described above, the external device may include the programmer 828 (shown in FIG. 8) and/or the workstation 1010 (shown in FIG. 10).

The horizontal axis 458 in FIG. 4 represents time and the vertical axis 460 represents the numerical values of the physiological parameter being monitored. In one embodiment, the values 400-426 represent the measured numerical value of the physiological parameter that is determined for each cardiac cycle 428-454 in the set 456 of cardiac cycles. For example, the first value 400 corresponds to a first measured value of a physiological parameter, such as the QRS amplitude 242, in a first cardiac cycle 428; the second value 402 corresponds to a second measured value of the QRS amplitude 242 in a second cardiac cycle 430; and so on, with the fourteenth value 426 corresponding to the QRS amplitude 242 in the fourteenth cardiac cycle 454. Alternatively, each value 400-426 may correspond to a combination of measured values of physiological parameters. By way of example only, the values 400-426 may each represent an average, sum, maximum, minimum, deviation, and the like, of two or more measured values of physiological parameters.

First and last cardiac cycles in the set of cardiac cycles are identified at 304. With respect to FIG. 4, the first cardiac cycle in the set 456 is identified as the cardiac cycle 428 and the last cardiac cycle in the set 456 is identified as the cardiac cycle 454. A reversal point counter is set to a numerical value of zero at 306. The reversal point counter is used to iteratively count the number of reversal points in a set of cardiac cycles in one embodiment, as described below. The reversal point counter is initially set to a value of zero prior to counting the reversal points in the set. A heartbeat counter is initialized to a numerical value of one at 308. The heartbeat counter is used to iteratively step through the cardiac cycles 428-454 in the set 456 as the various values 400-426 are compared to one another, as described below. The heartbeat counter is initially set to a value of one prior to beginning to step through the cardiac cycles 428-454 the set 456.

The process 300 proceeds by stepping through the values 400-426 of the physiological parameter measured during the cardiac cycles 428-454 in the set 456 and determining whether each of the values 400-426 constitutes a reversal point. A reversal point (RP) represents a value of the physiological parameter that exceeds the values of the physiological parameter in at least one prior and at least one subsequent cardiac cycle. A reversal point also includes a value of a physiological parameter that is less than the values of the physiological parameter in at least one prior and at least one subsequent cardiac cycle. The prior and subsequent cardiac cycles may be the cardiac cycles that are immediately prior to and immediately subsequent to a current cardiac cycle that represents a reversal point.

At 310, a determination is made as to whether the value of a physiological parameter in a current cardiac cycle is greater than the values of the physiological parameter in both prior and subsequent cardiac cycles. The value of the physiological parameter that was measured during the current cardiac cycle may be denoted by $Bt_x$, the value of the physiological parameter for the prior cardiac cycle may be denoted by $Bt_{x-1}$ and the value of the physiological parameter for the subsequent cardiac cycle may be denoted by $Bt_{x+1}$. The heartbeat counter may indicate which cardiac cycle 428-454 in the set 456 currently is being examined to determine whether the value of the physiological parameter in that cardiac cycle is a reversal point. For example, if the heartbeat counter is set to the initial value of one, then the current cardiac cycle is the first cardiac cycle 428. As shown in FIG. 4, the first value 400 of the physiological parameter is measured during the first cardiac cycle 428. The first value 400 is compared to the value of the physiological parameter of the cardiac cycle before the first cardiac cycle 428 and to the value of the physiological parameter of the cardiac cycle after the first cardiac cycle 428. As there is no cardiac cycle prior to the first cardiac cycle 428 in the set 456, the first value 400 is determined to not exceed the values of the physiological parameter prior to and after the first cardiac cycle 428 at 310.

Conversely, if the current cardiac cycle is associated with a value of the physiological parameter that exceeds the values of the physiological parameter that were measured in prior and subsequent cardiac cycles, then the value of the current cardiac cycle is determined to be a reversal point at 310. For example, if the current cardiac cycle is the second cardiac cycle 430, the second value 402 that corresponds to the second cardiac cycle 430 is found to exceed the first and third values 400, 404 of the physiological parameter that were obtained during the prior and subsequent cardiac cycles 400, 404. Accordingly, the second value 402 is determined to be a reversal point at 310.

If the value of the physiological parameter that is associated with the current cardiac cycle is not found to exceed the values of the physiological parameter in prior and subsequent cardiac cycles at 310, a determination is made as to whether the value associated with the current cardiac cycle is less than the values of the physiological parameter in prior and subsequent cardiac cycles at 312. For example, if the current cardiac cycle is the first cardiac cycle 428, the first value 400 is compared to the value of the physiological parameter of the cardiac cycle before the first cardiac cycle 428 and to the value of the physiological parameter of the cardiac cycle after the first cardiac cycle 428. As there is no cardiac cycle prior to the first cardiac cycle 428 in the set 456, the first value 400 is determined to not be less than the values of the physiological parameter prior to and after the first cardiac cycle 428 at 310.

Conversely, if the value of the physiological parameter associated with the current cardiac cycle is found to be less than the values of the physiological parameter obtained during prior and subsequent cardiac cycles, then the current cardiac cycle is determined to be a reversal point. For example, if the current cardiac cycle is the third cardiac cycle 432, the third value 404 is compared to the second and fourth values 402, 406 of the second and fourth cardiac cycles 430, 434. As the third value 404 is less than the second and fourth values 402, 406, the third value 404 is determined to be a reversal point at 312.

The reversal point counter is incremented by one if the value of the current cardiac cycle is determined to be a reversal point at 310 or 312. For example, if the value of the current cardiac cycle is found be a reversal point at 310, a numerical value of one is added to the reversal point counter to indicate that one more reversal point is found in the values 400-426 associated with the cardiac cycles 428-454 in the set 456.

At 314, a determination is made as to whether the current cardiac cycle is the last cardiac cycle. For example, a determination is made as to whether the current cardiac cycle is the final cardiac cycle in the set 456 of cardiac cycles 428-454. The heartbeat counter may be used to determine whether all cardiac cycles have been iteratively stepped through. For example, the heartbeat counter may be compared to a stored total number of cardiac cycles in the set 456. In the illustration shown in FIG. 4, a total of fourteen cardiac cycles 428-454 are in the set 456. At 314, if the heartbeat counter is not equal to the total number of cardiac cycles 428-454 in the set 456, then it is determined that the current cardiac cycle is not the last cardiac cycle. Alternatively, if at 314 the heartbeat counter current is equal to the total number of cardiac cycles 428-454 in the set 456, then the current cardiac cycle is determined to be the last cardiac cycle.

The heartbeat counter is incremented by one at 316. For example, after it is determined that the current cardiac cycle is not the last cardiac cycle in the set of cardiac cycles at 314, the heartbeat counter is increased by one at 316 and the process 300 shown in FIG. 3 returns to 310. If the current cardiac cycle is found to be the last cardiac cycle in the set at 314, the process 300 saves the number of reversal points and cardiac cycles in the set at 320. For example, the numerical values of the heartbeat counter and the reversal point counter may be stored in a computer-readable storage medium such as a computer readable memory. By way of example only, the heartbeat and reversal point counters may be stored in a memory 826 (shown in FIG. 8) of the IMD 100 (shown in FIG. 1), a memory of the external device 828 (shown in FIG. 8), and/or a memory of the workstation 1010 (shown in FIG. 10).

Applying the process 300 to the illustration shown in FIG. 4 reveals that a total of twelve reversal points are found in the set 456 of cardiac cycles 428-454, with all but the first and last values 400, 426 representing a reversal point. The first and last values 400, 426 do not constitute reversal points as the first and last values 400, 426 do not have at least one prior and at least one subsequent value that both exceed, or are both less than, each of the first and last values 400, 426. Each one of the values 402-424 has prior and subsequent values that are both greater than, or both less than, the value 402-424. For example, the second value 402 that is measured during the second cardiac cycle 430 is greater than the first and third values 400, 404 that are measured during the first and third cardiac cycles 428, 432. In another example, the seventh value 412 that is measured during the seventh cardiac cycle 440 is less than the sixth and eighth values 410, 414 that are measured during the sixth and eighth cardiac cycles 438, 442.

Figure 5:
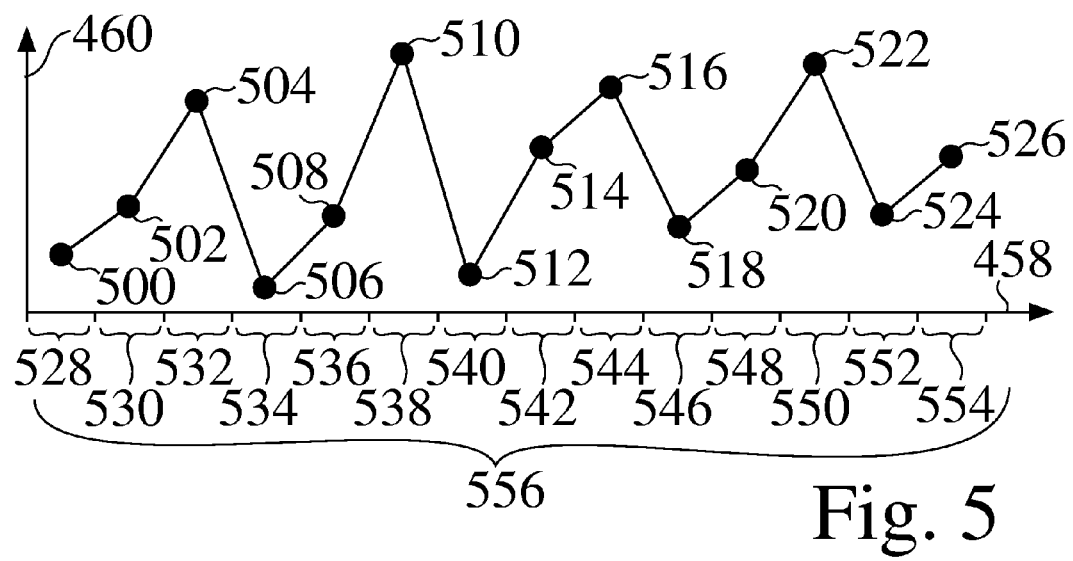
FIG. 5 is a graphic illustration of a different group of values measured for a physiological parameter during each cardiac cycle in a set of the cardiac cycles.

FIG. 5 is a graphic illustration of a different group of values 500-526 measured for a physiological parameter during each cardiac cycle 528-554 in a set 556 of the cardiac cycles. Similar to the values 400-426 (shown in FIG. 4) measured for a physiological parameter during the cardiac cycles 428-454 (shown in FIG. 4) in the set 456 (shown in FIG. 4), the values 500-526 vary with respect to the cardiac cycles 528-554 and the horizontal time axis 458. In contrast to the values 400-426, the values 500-526 do not regularly alternate between large and small numerical values with respect to the horizontal time axis 458. While each value 402-424 measured during the cardiac cycles 430-452 constitutes a reversal point, as described above, less than all of the values 502-524 constitute reversal points. Only the values 504, 506, 510, 512, 516, 518, 522, 524 may be found to be reversal points according to the process 300 (shown in FIG. 3).

For example, according to the process 300 described above, only the values 504, 510, 516, 522 are preceded and followed by cardiac cycles associated with lower values. The value 504 is preceded and followed by the lower values 502, 506 that were obtained during the prior and subsequent cardiac cycles 532, 534. The value 510 is preceded and followed by the lower values 508, 512 that were measured during the prior and subsequent cardiac cycles 536, 540. The value 516 is preceded and followed by the lower values 514, 518 that were obtained during the prior and subsequent cardiac cycles 542, 546. The value 522 is preceded and followed by the lower values 520, 524 that were measured during the prior and subsequent cardiac cycles 548, 552. In another example, only the values 506, 512, 518, 524 are preceded and followed by cardiac cycles associated with greater values. The value 506 is preceded and followed by the greater values 504, 508 that were obtained during the prior and subsequent cardiac cycles 532, 536. The value 512 is preceded and followed by the greater values 510, 514 that were measured during the prior and subsequent cardiac cycles 538, 542. The value 518 is preceded and followed by the greater values 516, 520 that were obtained during the prior and subsequent cardiac cycles 544, 548. The value 524 is preceded and followed by the greater values 522, 526 that were measured during the prior and subsequent cardiac cycles 550, 554.

In another embodiment, a reversal point is identified by comparing differences in the values of physiological parameters between consecutive cardiac cycles. For example, each of the values 400-426 shown in FIG. 4 may represent a difference between the values of a physiological parameter measured in a plurality of cardiac cycles. By way of example only, the first value 400 may represent a difference between the value of a physiological parameter measured during the first cardiac cycle 428 and the value of the physiological parameter measured during a cardiac cycle (not shown) occurring before the first cardiac cycle 428. Similarly, the second value 402 may represent the difference between the values of the physiological parameter measured during the second and first cardiac cycles 430, 428. The third value 404 may represent the difference between the values of the physiological parameter measured during the third and second cardiac cycles 432, 430, and the like. In such an embodiment, a reversal point may be found where a difference between the physiological parameter values for a current cardiac cycle and an immediately preceding cardiac cycle is greater than (a) the difference between the physiological parameter values measured for a plurality of cardiac cycles occurring before the current cardiac cycle and (b) the difference between the physiological parameter values measured for a plurality of cardiac cycles occurring after the current cardiac cycle. Similarly, a reversal point may be found where a difference between the physiological parameter values for a current cardiac cycle and an immediately preceding cardiac cycle is less than (a) the difference between the physiological parameter values measured for a plurality of cardiac cycles occurring before the current cardiac cycle and (b) the difference between the physiological parameter values measured for a plurality of cardiac cycles occurring after the current cardiac cycle.

Figure 6:
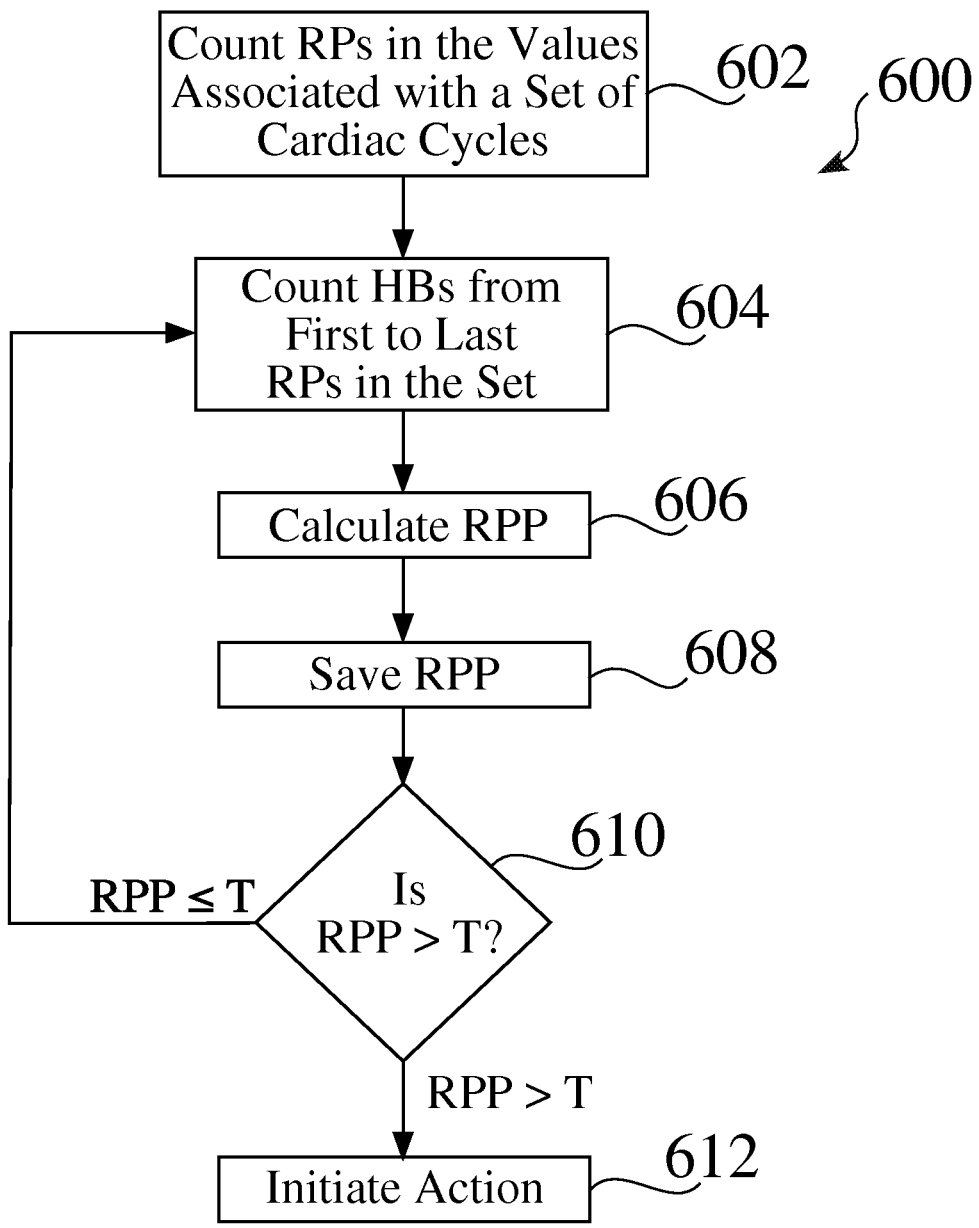
FIG. 6 illustrates a process for identifying myocardial instability.

FIG. 6 illustrates a process 600 for identifying myocardial instability. The process 600 may be used to determine if an action should be taken in response to the number of reversal points found in the values of a physiological parameter that correspond to a set of cardiac cycles. The process 600 may be performed in whole or part by a variety of devices and systems including the IMD 100 (shown in FIG. 1) and devices communicatively coupled with the IMD 100. For example, the actions described below in connection with the process 600 may be performed by the external device 828 (shown in FIG. 8) and/or the operator workstation 1010 (shown in FIG. 10).

At 602, the number of reversal points (RP) in the values associated with a set of cardiac cycles is counted. For example, the number of reversal points may be determined by analyzing a group of values of a physiological parameter that are measured during a set of cardiac cycles. The reversal points may be counted using the process 300 (shown in FIG. 3) described above. In one embodiment, the number of reversal points may be obtained from the reversal point counter described above.

The total number of heartbeats (HB) from the first to the last reversal points in the set of cardiac cycles is determined at 604. For example, the number of cardiac cycles from the first reversal point found in the set of cardiac cycles to the last reversal point found in the set is counted at 604. The number of cardiac cycles includes the cardiac cycles at which the first and last reversal points occur. By way of example only, the number of heartbeats from the first to last reversal points for the values 400-426 illustrated in FIG. 4 is twelve, with the first reversal point occurring at the second cardiac cycle 430 (shown in FIG. 4) and the last reversal point occurring at the thirteenth cardiac cycle 452 (shown in FIG. 4). In another example, the number of heartbeats from the first to last reversal points for the values 500-526 illustrated in FIG. 5 is eleven, with the first reversal point occurring at the third cardiac cycle 532 (shown in FIG. 5) and the last reversal point occurring at the thirteenth cardiac cycle 552 (shown in FIG. 5).

A reversal point percentage ("RPP") is calculated at 606. The reversal point percentage is a relation of a number of reversal points counted in a set of cardiac cycles and a number of heartbeats, or cardiac cycles, in the set of cardiac cycles. The reversal point percentage may be based on a ratio between the number of reversal points counted at 602 to the number of heartbeats counted at 604. In one embodiment, the reversal point percentage may be defined by the following relationship:

$$RPP = \frac{RP - 2}{HB - 2} \quad \text{(Eqn. 1)}$$

where RPP is the reversal point percentage for a set of cardiac cycles, RP is the number of reversal points in the set of cardiac cycles, as determined at 602, and HB is the number of heartbeats, or cardiac cycles, from the first reversal point to the last reversal point in the set of cardiac cycles, as determined at 604. The RPP may be expressed as a value between zero and one, as the RPP would be according to Equation 1. Alternatively, the value of the RPP may be multiplied by 100 to obtain a percentage value between zero and 100 percent. As shown in Equation 1, a quantitative value of two is subtracted from the numerator (e.g., RP) and from the denominator (e.g., HB) to account for the first and last cardiac cycles in the set of cardiac cycles. As the first and last cardiac cycles occur at the beginning or end of the set of cardiac cycles, the values of the physiological parameters associated with the first and last cardiac cycles may not be counted as reversal points. For example, the first and last cardiac cycles may not be counted as a reversal point because neither of the first and last cardiac cycles in the set are preceded and followed by cardiac cycles with greater values than the first or last cardiac cycle. Also, the first and last cardiac cycles are not preceded and followed by cardiac cycles having lesser values than the first or last cardiac cycle. Alternatively, a different quantitative value is added or subtracted from the numerator and/or denominator in Equation 1. In another embodiment, no number is added to or subtracted from the numerator or denominator of Equation 1.

With respect to FIG. 4, the reversal point percentage calculated from the values 400-426 is 1 according to the embodiment described above. For example, each of the values 402-424 is a reversal point in the set 456 of cardiac cycles 428-454. Thus, there are twelve reversal points in the values 400-426 and the numerator in Equation 1 above is 12-2, or 10. The first reversal point is the second value 402, which occurs during the second cardiac cycle 430, and the last reversal point is the thirteenth value 424, which occurs during the thirteenth cardiac cycle 452, as described above. Thus, there are twelve cardiac cycles from the first reversal point to the last reversal point. Accordingly, the denominator in Equation 1 above is 12-2, or 10. Dividing the numerator of 10 by the denominator of 10 is 1, therefore the reversal point percentage for the values 400-426 measured during the set 456 of cardiac cycles 428-454 is 1, or 100%.

With respect to FIG. 5, the reversal point percentage calculated from the values 500-526 is ⅔, or approximately 0.67, according to the embodiment described above. For example, each of the values 504, 506, 510, 512, 516, 518, 522, 524 is a reversal point in the set 556 of cardiac cycles 528-554. Thus, there are eight reversal points in the values 500-526 and the numerator in Equation 1 above is 8-2, or 6. The first reversal point is the third value 504, which occurs during the third cardiac cycle 532, and the last reversal point is the thirteenth value 524, which occurs during the thirteenth cardiac cycle 552, as described above. Thus, there are eleven cardiac cycles from the first reversal point to the last reversal point. Accordingly, the denominator in Equation 1 above is 11-2, or 9. Dividing the numerator of 6 by the denominator of 9 is ⅔, or approximately 0.67, therefore the reversal point percentage for the values 500-526 measured during the set 556 of cardiac cycles 528-554 is ⅔, or approximately 67%.

In one embodiment, the calculation of the reversal point percentage is corrected when premature ventricular contraction (PVC) occurs. For example, the calculation of the reversal point percentage for the values of a physiological parameter obtained during a set of cardiac cycles may be adjusted if PVC occurs during the set of cardiac cycles. The correction may include disregarding the values of the physiological parameter that were obtained during the same cardiac cycles in which PVC occurs. Alternatively, the correction may include disregarding the values of the physiological parameter that were obtained during the same cardiac cycles in which PVC occurs and disregarding the values obtained during the cardiac cycles preceding and subsequent to the cardiac cycles in which PVC occurs. In another embodiment, the correction includes replacing the values of the physiological parameter that were obtained during the same cardiac cycles in which PVC occurs with a function of one or more other values obtained during the set of cardiac cycles. By way of example only, the values may be replaced with one or more of a mean, average, maximum, minimum, deviation, and the like, of the values obtained during cardiac cycles in the set that occur before the cardiac cycles in which PVC occurs.

Returning to FIG. 6, the reversal point percentage is saved at 608. For example, the reversal point percentage may be stored in a computer-readable storage medium such as a computer readable memory for later access and retrieval. By way of example only, the reversal point percentage may be stored in the memory 826 (shown in FIG. 8). The reversal point percentage is compared to a predetermined threshold (T) at 610. The predetermined threshold may be stored and obtained from a computer-readable storage medium. The threshold represents a maximum reversal point percentage that may be calculated at 606 before a responsive action is taken. If the reversal point percentage that is calculated at 606 exceeds the threshold, an action may be taken at 608 to treat the patient or to notify a physician or other healthcare operator that the patient's heart 102 is exhibiting instable myocardial behavior. By way of example only, if the reversal percentage points calculated for the values 400-426 of FIG. 4 and the values 500-526 of FIG. 5 are compared to a threshold of 0.8, then only the values 400-426 of FIG. 4 would trigger a responsive action at 608. As described above, the reversal point percentage that may be calculated for the values 400-426 is 1 and the reversal point percentage that may be calculated for the values 500-526 is approximately 0.67. As only the reversal point percentage of 1 exceeds the threshold of 0.8, only the values 400-426 would initiate a responsive action.

The responsive action taken at 608 may include initiating stimulation therapy of the heart 102 using the IMD 100, including pacing stimulation. For example, the determination that a reversal point percentage exceeds a threshold at 610 may be used to trigger a responsive action to an arrhythmia. The action may include activating an audible and/or visual alarm to inform a physician of the unstable myocardial behavior that has been detected. For example, a speaker 910 (shown in FIG. 9) of the external device 828 (shown in FIG. 8) may be activated to produce an audible sound or tone 942 (shown in FIG. 9). In another example, a display 922 (shown in FIG. 9) of the external device 828 may produce an output on a video display 932 (shown in FIG. 9) that indicates that unstable myocardial behavior is detected.

On the other hand, if the reversal point percentage does not exceed the threshold at 610, then the process 600 returns to 602 where the reversal points in another set of cardiac cycles is counted. The process 600 therefore may continue in a loop-wise manner to count the number of reversal points in multiple sets of cardiac cycles and, based thereon, monitor the patient's heart 102 for unstable myocardial behavior. The reversal point percentage may be calculated for each of several sets of cardiac cycles. The sets of cardiac cycles may be consecutive, where no cardiac cycles are common to multiple sets of the cardiac cycles, or the sets may be overlapping, where multiple cardiac cycles have at least one cardiac cycle in common. Continually measuring the reversal point percentages for multiple consecutive or overlapping sets of cardiac cycles may permit a physician to monitor the onset of myocardial instability or an increase in a level or amount of myocardial instability. For example, a first reversal point percentage may be calculated for a first set of twelve cardiac cycles, a second reversal point percentage may be calculated for a second set of twelve cardiac cycles, and so on. In such an example, the first reversal point percentage is calculated for the first through twelfth cardiac cycles, the second reversal point percentage is calculated for the thirteenth through twenty-fourth cardiac cycles, and so on. Alternatively, the reversal point percentage is repeatedly calculated for a moving window of cardiac cycles. For example, the reversal point percentage may be calculated for each of multiple cardiac cycles that overlap one another. By way of example only, a first reversal point percentage may be calculated for the values of a physiological parameter obtained during first through tenth cardiac cycles; a second reversal point percentage is calculated for the values of the physiological parameter obtained during fifth through fifteenth cardiac cycles; a third reversal point percentage is calculated for the values obtained during tenth through twentieth cardiac cycles; and the like. The number of cardiac cycles that are in common with consecutive windows of cardiac cycles may be as few as a single cardiac cycle to as many as N−1 cardiac cycles, where N is the number of cardiac cycles in each window of cardiac cycles.

Figure 7:
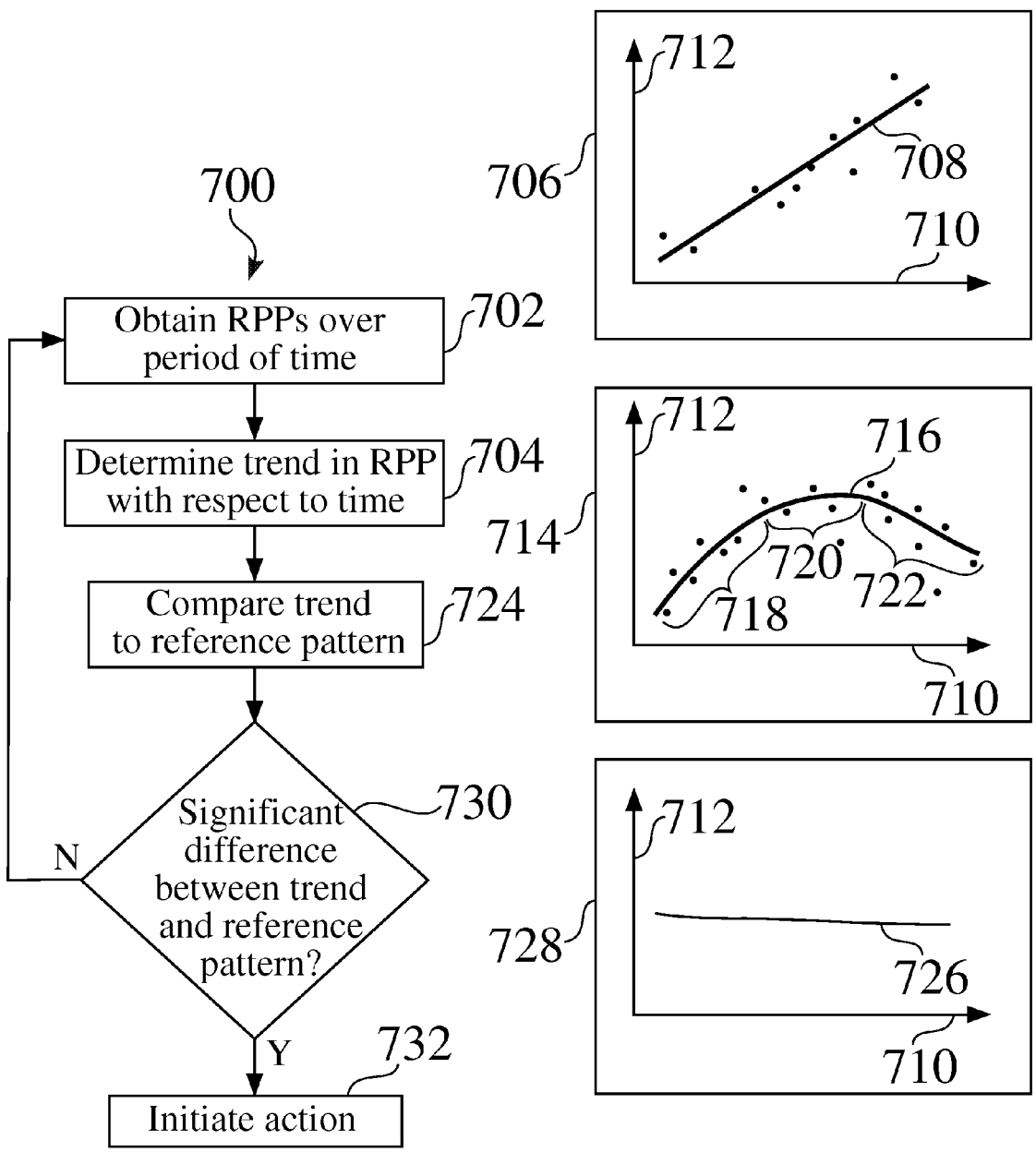
FIG. 7 illustrates a process for monitoring reversal point percentages that are calculated for multiple sets of cardiac cycles over a given time period.

FIG. 7 illustrates a process 700 for monitoring reversal point percentages that are calculated for multiple sets of cardiac cycles over a given time period. The process 700 may be used to monitor for a trend in the reversal point percentages measured for the multiple sets of cardiac cycles over an extended period of time, such as a week, a month, several months, a year, and the like. The process 700 may be performed in whole or part by a variety of devices and systems including the IMD 100 (shown in FIG. 1) and devices communicatively coupled with the IMD 100. For example, the actions described below in connection with the process 700 may be performed by the external device 828 (shown in FIG. 8) and/or the operator workstation 1010 (shown in FIG. 10).

At 702, several reversal point percentages are obtained. The reversal point percentages are the reversal point percentages that are based on the values of a physiological parameter measured over a period of time. For example, the reversal point percentages that are obtained at 702 may include the reversal point percentages that were calculated for a patient over the preceding month. The reversal point percentages may be obtained from a computer readable storage medium such as a computer memory. For example, the reversal point percentages may be obtained from the memory 826 (shown in FIG. 8) of the IMD 100 (shown in FIG. 1).

A trend in the reversal point percentages with respect to time is determined at 704. The trend may be determined by comparing increases, decreases or other relationships between the reversal point percentages with respect to the time period over which the reversal point percentages were obtained. The trend may be graphically displayed on a display device such as the display 922 (shown in FIG. 9) or the video display 932 (shown in FIG. 9) of the external device 828 (shown in FIG. 8). A first graphical inset 706 illustrates an example of a first trend 708 between reversal point percentages and time. The horizontal axis 710 in the inset 706 represents the time period over which the reversal point percentages were obtained and the vertical axis 712 represents the numerical values of the reversal point percentages. The reversal point percentages are plotted as a scatter plot in the first inset 706. The reversal point percentages in the first inset 706 demonstrate an increasing trend 708 with respect to time. By way of example only, the trend 708 may be determined using a statistical function or model, such as a least squares model, a weighted least squares model, an R-squared model, an autoregressive moving average model, or a generalized linear or nonlinear model. The first trend 708 shows a continually increasing trend in the reversal point percentages with respect to time. As described below, the first trend 708 may represent a heart 102 demonstrating increasing myocardial instability with respect to time.

A second graphical inset 714 illustrates an example of a second trend 716 between reversal point percentages and time. In contrast to the first trend 708, the second trend 716 does not show a continual increase in the reversal point percentages with respect to time. The second trend 716 shows an initial increase 718, a leveling off portion 720, followed by a decreasing portion 722. As described below, the second trend 716 may represent a heart 102 that demonstrates increasing myocardial stability with respect to time.

The trend that is determined at 704 is compared to a reference pattern at 724. The reference pattern may be a relationship between the reversal point percentages and time that is compared to the trend in order to determine whether the patient is exhibiting instable myocardial behavior. For example, the reference pattern may include a desired relationship 726 between the reversal point percentages and time, as shown in the third graphical inset 728. The trend that is determined 704 is compared to the reference pattern and the amount of deviation of the trend from the reference pattern is analyzed at 730. If the amount of deviation between the trend and the reference pattern is found to be significant at 730, the process 700 may determine that the heart 102 is exhibiting instable myocardial behavior. If the amount of deviation is found to be insignificant at 730, the process 700 may determine that the heart 102 is exhibiting stable myocardial behavior. The amount of deviation between the trend and the reference pattern may be calculated using a statistical function or method, such as a root mean square analysis, for example. The significance of the amount of deviation may be established by comparing the amount of deviation to a threshold. The amount of deviation that is compared to the threshold may be the maximum amount of deviation over the period of time over which the trend is determined at 704. Alternatively, the amount of deviation that is compared to the threshold may be the summed total of the amount of deviation during the period of time over which the trend is determined at 704, or over a subset of the period of time. If the amount of deviation exceeds the threshold, then the amount of deviation may be significant. On the other hand, if the amount of deviation does not exceed the threshold, then the amount of deviation may not be significant.

If the amount of deviation between the trend in the reversal point percentages and the reference pattern is found to be significant at 730, a responsive action is taken at 732. For example, an action to treat the patient or to notify a physician or other healthcare operator that the patient's heart 102 is exhibiting instable myocardial behavior may be initiated. The action taken at 732 may include initiating stimulation therapy of the heart 102 using the IMD 100, including pacing stimulation. The action may include activating an audible and/or visual alarm to inform a physician of the unstable myocardial behavior that has been detected. For example, the speaker 910 (shown in FIG. 9) of the external device 828 (shown in FIG. 8) may be activated to produce an audible sound or tone 942 (shown in FIG. 9). In another example, the display 922 (shown in FIG. 9) of the external device 828 may produce an output on the video display 932 (shown in FIG. 9) that indicates that unstable myocardial behavior is detected. Alternatively, if the amount of deviation is found to be insignificant at 730, then no responsive action may be taken. For example, the process 700 may return to 702 in order to continue determining trends in the reversal point percentages and comparing the trends to a reference pattern, as described above.

Figure 8:
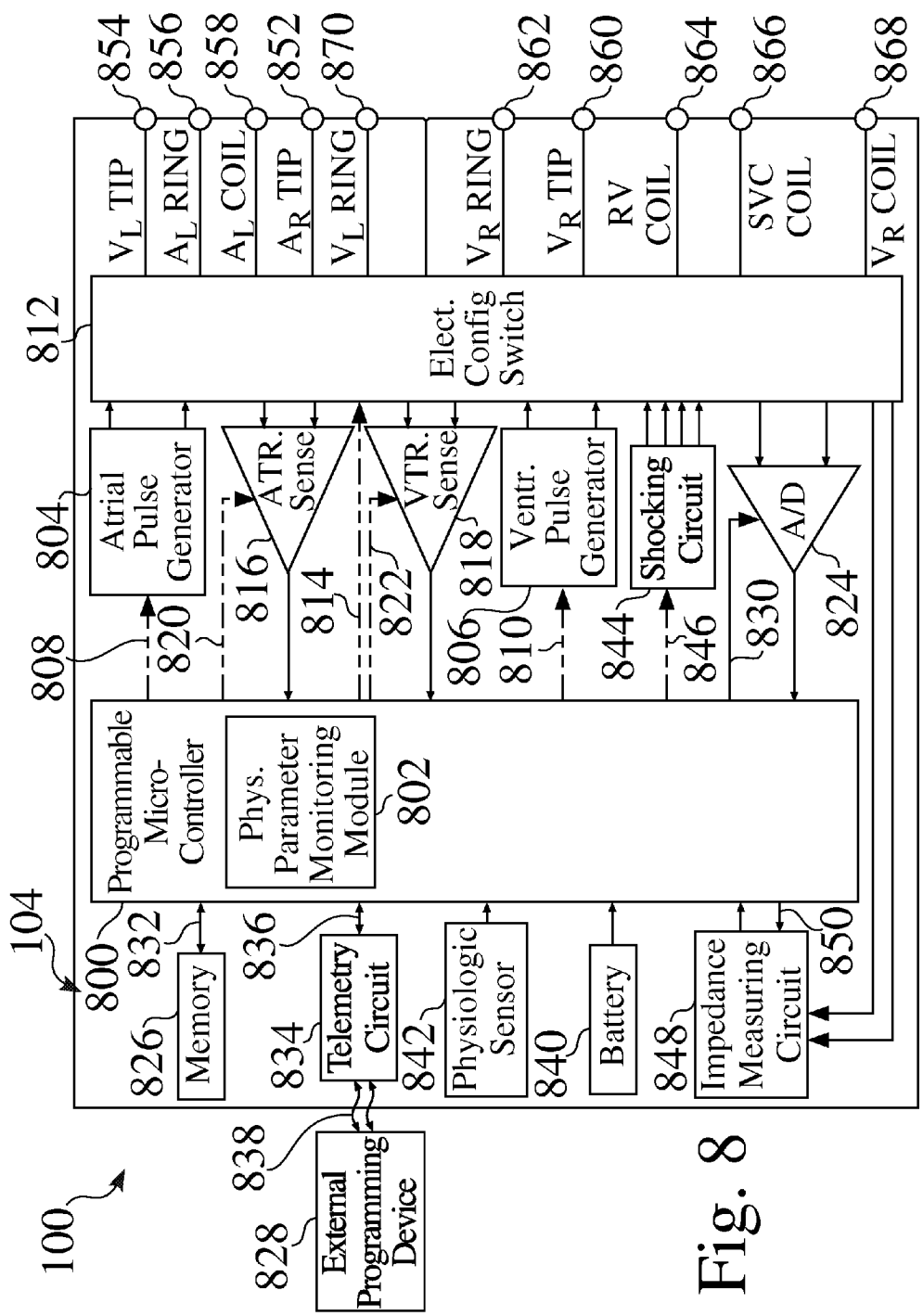
FIG. 8 illustrates a block diagram of exemplary internal components of the IMD shown in FIG. 1.

FIG. 8 illustrates a block diagram of exemplary internal components of the IMD 100. The IMD 100 is for illustration purposes only, and it is understood that the circuitry could be duplicated, eliminated or disabled in any desired combination to provide a device capable of treating the appropriate chamber(s) of the heart with cardioversion, defibrillation and/or pacing stimulation. As described above, the IMD 100 may be used to sense cardiac signals used to derive the values 400-426 (shown in FIG. 4), 500-526 (shown in FIG. 5), for example. The IMD 100 may perform one or more of the actions described above in connection with the processes 300 (shown in FIG. 3), 600 (shown in FIG. 6), 700 (shown in FIG. 7).

The housing 104 for IMD 100 (shown schematically in FIG. 8), is often referred to as the "can", "case" or "case electrode" and may be programmably selected to act as the return electrode for all "unipolar" modes. The housing 104 further includes a connector (not shown) having a plurality of terminals, namely a right atrial tip terminal ($A_R$ TIP) 852, a left ventricular tip terminal ($V_L$ TIP) 854, a left atrial ring terminal ($A_L$ RING) 856, a left atrial shocking terminal ($A_L$ COIL) 858, a right ventricular tip terminal ($V_R$ TIP) 860, a right ventricular ring terminal ($V_R$ RING) 862, a right ventricular shocking terminal (RV COIL) 864, an SVC shocking terminal (SVC COIL) 866, a right ventricular coil terminal ($V_R$ COIL) 868 and a left ventricular ring terminal ($V_L$ RING) 870.

The IMD 100 includes a programmable microcontroller 800, which controls the operation of the IMD 100 based on acquired cardiac signals. The microcontroller 800 (also referred to herein as a processor module or unit) typically includes a microprocessor, or equivalent control circuitry, is designed specifically for controlling the delivery of stimulation therapy and may further include RAM or ROM memory, logic and timing circuitry, state machine circuitry, and I/O circuitry. Typically, the microcontroller 800 includes the ability to process or monitor input signals (e.g., data) as controlled by a program code stored in a memory. Among other things, the microcontroller 800 receives, processes, and manages storage of digitized data from the various electrodes 124-138 (shown in FIG. 1). The microcontroller 800 may also analyze the data, for example, in connection with collecting, over a period of time, values of one or more physiological parameters, as described above, variations in a segment of interest and impedance vectors. A physiological parameter monitoring module 802 may monitor the values or variations in one or more physiological parameters. By way of example only, the physiological parameter monitoring module 802 may monitor the values or variations in one or more of cardiac signal waveforms such as the ST segment 232, 234 (shown in FIG. 2) and the R-wave 212, 214 (shown in FIG. 2), as described above.

The IMD 100 includes an atrial pulse generator 804 and a ventricular/impedance pulse generator 806 to generate pacing stimulation pulses. In order to provide stimulation therapy in each of the four chambers of the heart 102 (shown in FIG. 1), the atrial and ventricular pulse generators 804 and 806, may include dedicated, independent pulse generators, multiplexed pulse generators, or shared pulse generators. The pulse generators, 804 and 806, are controlled by the microcontroller 800 via appropriate control signals, 808 and 810, respectively, to trigger or inhibit the stimulation pulses.

Switch 812 includes a plurality of switches for connecting the desired electrodes, including the electrodes 124 through 138 (shown in FIG. 1), to the appropriate I/O circuits, thereby providing complete electrode programmability. The switch 812, in response to a control signal 814 from the microcontroller 800, determines the polarity of stimulation pulses (e.g., unipolar, bipolar, etc.) by selectively closing the appropriate combination of switches (not shown) as is known in the art. Atrial sensing circuits 816 and ventricular sensing circuits 818 may also be selectively coupled to the leads 114, 116 and 118 (shown in FIG. 1) through the switch 812 for detecting the presence of cardiac activity in each of the four chambers of the heart 102 (shown in FIG. 1). Control signals 820 and 822 from microcontroller 800 direct output of the atrial and ventricular sensing circuits 816 and 818 that are connected to the microcontroller 800. In this manner, the atrial and ventricular sensing circuits 816 and 818 are able to trigger or inhibit the atrial and ventricular pulse generators 804 and 810.

The cardiac signals are applied to the inputs of an analog-to-digital (A/D) data acquisition system 824. The data acquisition system 824 is configured to acquire IEGM signals, convert the raw analog data into a digital IEGM signals, and store the digital IEGM signals in a memory 826 for later processing and/or telemetric transmission to an external device 828. The memory 826 may be embodied in a computer-readable storage medium such as a ROM, RAM, flash memory, or other type of memory. The microcontroller 800 is coupled to the memory 826 by a suitable data/address bus 832, wherein the programmable operating parameters used by the microcontroller 800 are stored and modified, as required, in order to customize the operation of IMD 100 to suit the needs of a particular patient. The memory 826 also may store data indicative of myocardial function, such as the IEGM data, ST segment shifts, reference ST segment shifts, ST segment shift thresholds, R wave amplitudes, R wave amplitude changes, impedance vectors, trend information associated with ischemic episodes, and the like for a desired period of time (e.g., 6 hours, 12 hours, 18 hours or 24 hours, and the like). The memory 826 may store the values of the physiological parameters being monitored by the physiological parameter monitoring module 802. The values of the physiological parameters may be communicated to the external device 828 for analysis in accordance with one or more of the processes described above. Alternatively, the microcontroller 800 may perform one or more of the analyses described in the processes above and output the results of the processes to the external device 828. The memory 826 may store one or more of the reversal points, the reversal point percentages, the heartbeat counter, the reversal point counter, and the thresholds described above.

A control signal 830 from the microcontroller 800 determines when the A/D 824 acquires signals, stores the signals in the memory 826, or transmits data to the external device 828. The A/D 824 is coupled to the right atrial lead 116 (shown in FIG. 1), the coronary sinus lead 118 (shown in FIG. 1), and the right ventricular lead 114 through the switch 812 to sample cardiac signals across any combination of desired electrodes 124-138 (shown in FIG. 1).

The operating parameters of the IMD 100 may be non-invasively programmed into the memory 826 through a telemetry circuit 834 in communication with the external device 828, such as another external device, a trans-telephonic transceiver or a diagnostic system analyzer. The telemetry circuit 834 is activated by the microcontroller 800 by a control signal 836. The telemetry circuit 834 allows intra-cardiac electrograms, and status information relating to the operation of IMD 100 (as contained in the microcontroller 800 or memory 826), to be sent to the external device 828 through an established communication link 838. The IMD 100 additionally includes a battery 840, which provides operating power to all of the circuits shown within the housing 104, including the microcontroller 800. The IMD 100 also includes a physiologic sensor 842 that may be used to adjust pacing stimulation rate according to the exercise state of the patient. The physiologic sensor 842 may be used to monitor the values of one or more physiological parameters, as described above.

In the case where IMD 100 is intended to operate as an ICD device, the IMD 100 detects the occurrence of a shift in one or more waveforms in detected cardiac signals that indicates an arrhythmia, and automatically applies an appropriate electrical shock therapy to the heart aimed at terminating the detected arrhythmia. To this end, the microcontroller 800 further controls a shocking circuit 844 by way of a control signal 846. The shocking circuit 844 generates shocking pulses of low (up to 0.5 joules), moderate (0.5-10 joules) or high energy (11 to 40 joules). Such shocking pulses are applied to the heart 102 (shown in FIG. 1) of the patient through at least two shocking electrodes, and as shown in this embodiment, selected from the left atrial coil electrode 128 (shown in FIG. 1), the RV coil electrode 134 (shown in FIG. 1), and/or the SVC coil electrode 138 (shown in FIG. 1).

The IMD 100 includes an impedance measuring circuit 848 which is enabled by the microcontroller 800 via a control signal 850. The impedance measuring circuit 848 may be electrically coupled to the switch 812 so that impedance at any desired electrode may be obtained.

Figure 9:
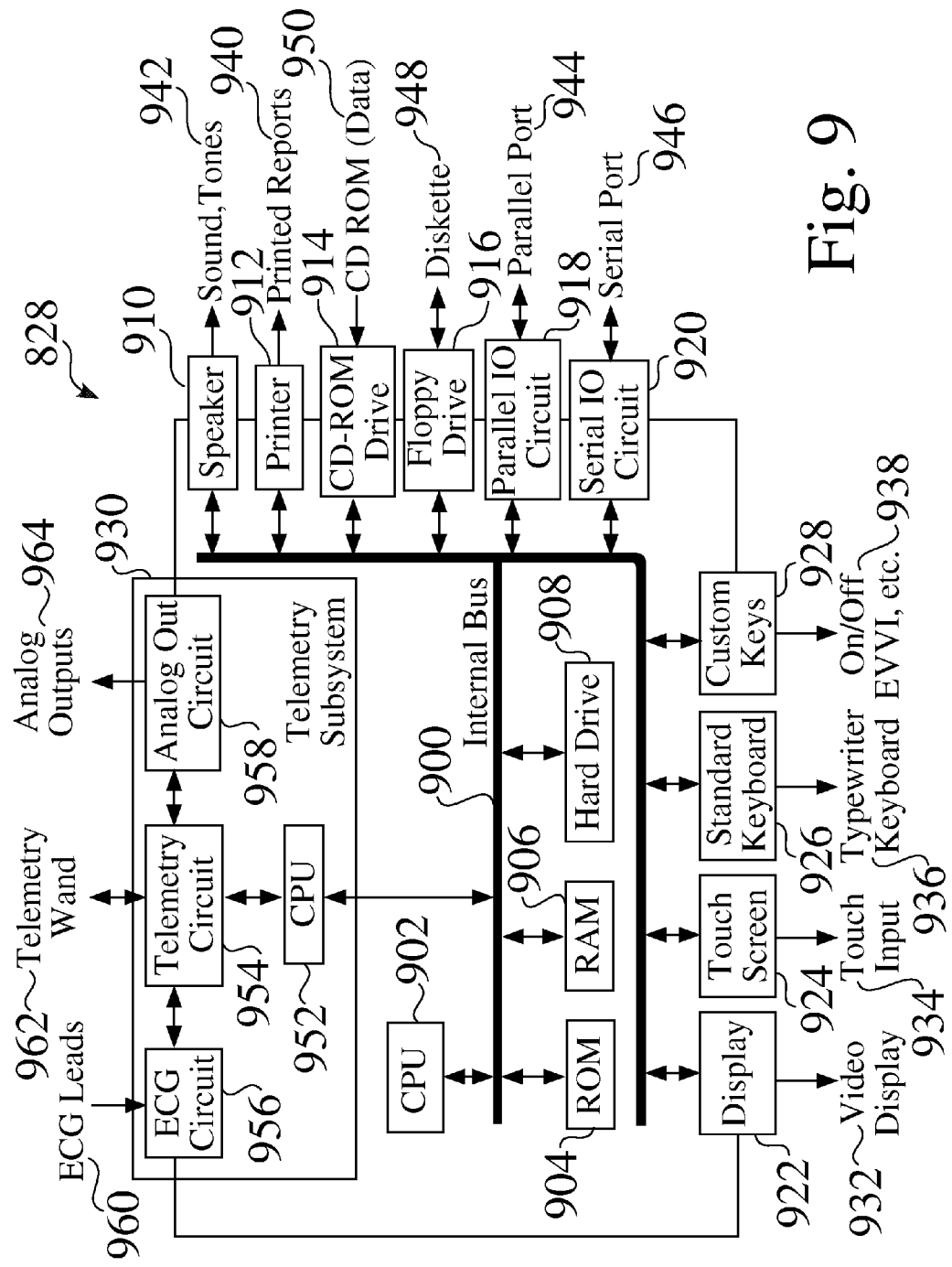
FIG. 9 illustrates a functional block diagram of an external device that is operated to interface with the IMD shown in FIG. 1.

FIG. 9 illustrates a functional block diagram of the external device 828, such as a programmer, that is operated by a physician, a health care worker, or a patient to interface with IMD 100 (shown in FIG. 1). As described above, the external device 828 may be used to determine the values 400-426 (shown in FIG. 4), 500-526 (shown in FIG. 5) based on cardiac signals measured by the IMD 100 (shown in FIG. 1), for example. The external device 828 may perform one or more of the actions described above in connection with the processes 300 (shown in FIG. 3), 600 (shown in FIG. 6), 700 (shown in FIG. 7). The external device 828 may be utilized in a hospital setting, a physician's office, or even the patient's home to communicate with the IMD 100 to change a variety of operational parameters regarding the therapy provided by the IMD 100 as well as to select among physiological parameters to be monitored and recorded by the IMD 100. For example, the external device 828 may be used to program coronary episode related parameters, such as ischemia-related and ST segment shift thresholds, duration thresholds, and the like. Further, the external device 828 may be utilized to interrogate the IMD 100 to determine the condition of a patient, to adjust the physiological parameters monitored or to adapt the therapy to a more efficacious one in a non-invasive manner. In one embodiment, the external device 828 is used to monitor the values of one or more physiological parameters to determine the presence of reversal points in the values and, based thereon, monitor the heart 102 for myocardial instability.

External device 828 includes an internal bus 900 that connects/interfaces with a Central Processing Unit (CPU) 902, ROM 904, RAM 906, a hard drive 908, the speaker 910, a printer 912, a CD-ROM drive 914, a floppy drive 916, a parallel I/O circuit 918, a serial I/O circuit 920, the display 922, a touch screen 924, a standard keyboard connection 926, custom keys 928, and a telemetry subsystem 930. The internal bus 900 is an address/data bus that transfers information (e.g., either memory data or a memory address from which data will be either stored or retrieved) between the various components described. The hard drive 908 may store operational programs as well as data, such as the values of the physiological parameters obtained by the IMD 100 (shown in FIG. 1), reversal points, reversal point percentages, heartbeat counters, reversal point counters, reversal point percentage thresholds, patterns that are compared to trends in the reversal point percentages, reference ST segments, ST thresholds, impedance thresholds, other thresholds, timing information and the like.

The CPU 902 typically includes a microprocessor, a microcontroller, or equivalent control circuitry, designed specifically to control interfacing with the external device 828 and with the IMD 100 (shown in FIG. 1). The CPU 902 may further include RAM or ROM memory, logic and timing circuitry, state machine circuitry, and I/O circuitry to interface with the IMD 100. Typically, the microcontroller 800 (shown in FIG. 8) includes the ability to process or monitor input signals (e.g., data) as controlled by program code stored in memory (e.g., ROM 904). For example, the microcontroller 800 may acquire values of physiological parameters that are measured by the IMD 100 and process the values according to one or more of the processes described herein. By way of example only, the microcontroller 800 may determine the number of reversal points in a group of values obtained during a set of cardiac cycles, the reversal point percentages for multiple sets of cardiac cycles, trends in the reversal point percentages, and the like, as described above.

The display 922 (e.g., may be connected to the video display 932) and the touch screen 924 display text, alphanumeric information, data and graphic information via a series of menu choices to be selected by the user relating to the IMD 100 (shown in FIG. 1), such as for example, status information, operating parameters, therapy parameters, patient status, access settings, software programming version, values of physiological parameters, reversal point counters, heartbeat counters, reversal point percentages, trends in the reversal point percentages, thresholds, and the like. The touch screen 924 accepts a user's touch input 934 when selections are made. The keyboard 926 (e.g., a typewriter keyboard 936) allows the user to enter data to the displayed fields, operational parameters, therapy parameters, as well as interface with the telemetry subsystem 930. Furthermore, custom keys 928 turn on/off 440 938 (e.g., EVVI) the external device 828. The printer 912 prints hard-copies of reports 940 for a physician/healthcare worker to review or to be placed in a patient file, and speaker 910 provides an audible warning (e.g., sounds and tones 942) to the user in the event a patient has any abnormal physiological condition occur while the external device 828 is being used. The parallel I/O circuit 918 interfaces with a parallel port 944. The serial I/O circuit 920 interfaces with a serial port 946. The floppy drive 916 accepts diskettes 948. The CD-ROM drive 914 accepts CD ROMs 950.

The telemetry subsystem 930 includes a central processing unit (CPU) 952 in electrical communication with a telemetry circuit 954, which communicates with both an ECG circuit 956 and an analog out circuit 958. The ECG circuit 956 is connected to ECG leads 960. The telemetry circuit 954 is connected to a telemetry wand 962. The analog out circuit 958 includes communication circuits, such as a transmitting antenna, modulation and demodulation stages (not shown), as well as transmitting and receiving stages (not shown) to communicate with analog outputs 964. The external device 828 may wirelessly communicate with the IMD 100 (shown in FIG. 1) and utilize protocols, such as Bluetooth, GSM, infrared wireless LANs, HIPERLAN, 3G, satellite, as well as circuit and packet data protocols, and the like. A wireless RF link utilizes a carrier signal that is selected to be safe for physiologic transmission through a human being and is below the frequencies associated with wireless radio frequency transmission. Alternatively, a hard-wired connection may be used to connect the external device 828 to IMD 100 (e.g., an electrical cable having a USB connection).

Figure 10:
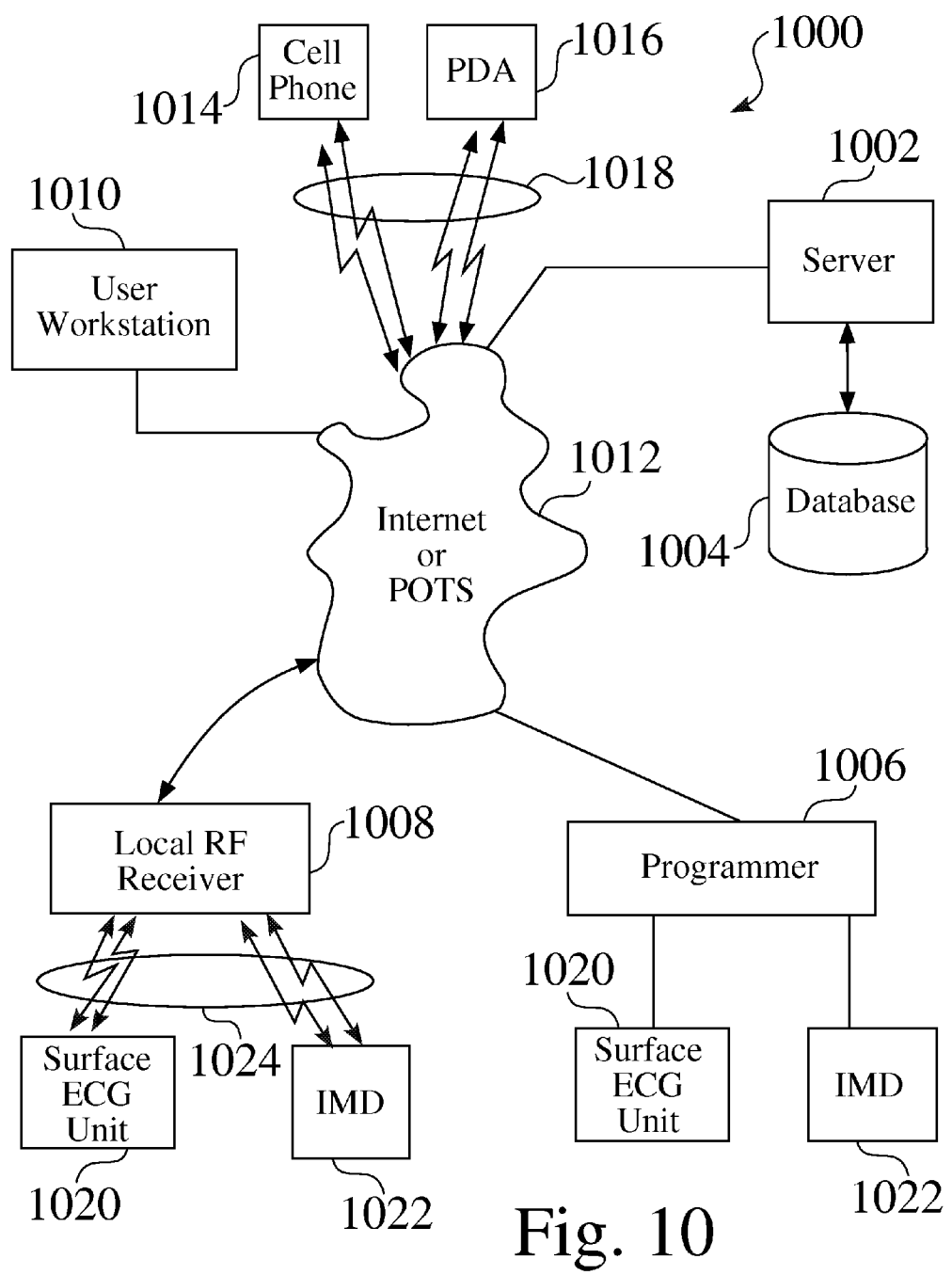
FIG. 10 illustrates a distributed processing system in accordance with one embodiment.

FIG. 10 illustrates a distributed processing system 1000 in accordance with one embodiment. The distributed processing system 1000 includes a server 1002 that is connected to a database 1004, a programmer 1006 (e.g., similar to external device 828 described above and shown in FIG. 8), a local RF transceiver 1008 and a user workstation 1010 electrically connected to a communication system 1012. The communication system 1012 may be the internet, a voice over IP (VoIP) gateway, a local plain old telephone service (POTS) such as a public switched telephone network (PSTN), and the like. Alternatively, the communication system 1012 may be a local area network (LAN), a campus area network (CAN), a metropolitan area network (MAN), or a wide area network (WAM). The communication system 1012 serves to provide a network that facilitates the transfer/receipt of cardiac signals, processed cardiac signals, histograms, trend analysis and patient status, and the like.

The server 1002 is a computer system that provides services to other computing systems (e.g., clients) over a computer network. The server 1002 acts to control the transmission and reception of information (e.g., cardiac signals, processed cardiac signals, values of physiological parameters, reversal points, reversal point percentages, heartbeat counters, reversal point counters, thresholds, trends in reversal point percentages, impedances, histograms, statistical analysis, trend lines, and the like). The server 1002 interfaces with the communication system 1012 to transfer information between the programmer 1006, the local RF transceiver 1008, the user workstation 1010 as well as a cell phone 1014, and a personal data assistant (PDA) 1016 to the database 1004 for storage/retrieval of records of information. For instance, the server 1002 may download, via a wireless connection 1018, to the cell phone 1014 or the PDA 1016 the results of processed cardiac signals, the processes and analyses described above, impedance vectors, or a patient's physiological state (e.g., is the patient is exhibiting instable myocardial behavior) based on previously recorded cardiac information. On the other hand, the server 1002 may upload raw cardiac signals (e.g., unprocessed cardiac data) from a surface ECG unit 1020 or an IMD 1022 via the local RF transceiver 1008 or the programmer 1006.

Database 1004 is any commercially available database that stores information in a record format in electronic memory. The database 1004 stores information such as raw cardiac data, processed cardiac signals (e.g. reversal points, reversal point counters, heartbeat counters, and the like), statistical calculations (e.g., reversal point percentages, averages, modes, standard deviations), histograms, cardiac trends (e.g., STS trends, trends in the reversal point percentages), and the like. The information is downloaded into the database 1004 via the server 1002 or, alternatively, the information is uploaded to the server from the database 1004.

The programmer 1006 is similar to the external device 828 shown in FIG. 8 and described above, and may reside in a patient's home, a hospital, or a physician's office. Programmer 1006 interfaces with the surface ECG unit 1020 and the IMD 1022 (e.g., similar to the IMD 100 described above and shown in FIG. 1). The programmer 1006 may wirelessly communicate with the IMD 1022 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 1006 to IMD 1022 (e.g., an electrical cable having a USB connection). The programmer 1006 is able to acquire cardiac signals from the surface of a person (e.g., ECGs), or the programmer is able to acquire intra-cardiac electrogram (e.g., IEGM) signals from the IMD 1022. The programmer 1006 interfaces with the communication system 1012, either via the internet or via POTS, to upload the cardiac data acquired from the surface ECG unit 1020 or the IMD 1022 to the server 1002. The programmer 1006 may upload more than just raw cardiac data. For instance, the programmer 1006 may upload status information, operating parameters, therapy parameters, patient status, access settings, software programming version, values of one or more physiological parameters, ST segment thresholds, calculated or measured impedance vectors, and the like.

The local RF transceiver 1008 interfaces with the communication system 1012, via a communication link 1024, to upload cardiac data acquired from the surface ECG unit 1020 or the IMD 1022 to the server 1002. In one embodiment, the surface ECG unit 1020 and the IMD 1022 have a bi-directional connection with the local RF transceiver via a wireless connection. The local RF transceiver 1008 is able to acquire cardiac signals from the surface of a person (e.g., ECGs), or acquire intra-cardiac electrogram (e.g., IEGM) signals from the IMD 1022. On the other hand, the local RF transceiver 1008 may download stored cardiac data from the database 1004 or the analysis of cardiac signals from the database 1004 (e.g., reversal point percentages, trends in reversal point percentages, and the like) information to the surface ECG unit 1020 or the IMD 1022.

The user workstation 1010 may interface with the communication system 1012 via the internet or POTS to download information via the server 1002 from the database 1004. Alternatively, the user workstation 1010 may download raw data from the surface ECG unit 1020 or IMD 1022 via either the programmer 1006 or the local RF transceiver 1008. Once the user workstation 1010 has downloaded the cardiac information (e.g., raw cardiac signals, values of physiological parameters, ST segments, impedance vectors, and the like), the user workstation 1010 may process the cardiac signals, determine reversal points, calculate reversal point percentages, determine trends in reversal point percentages, create histograms, calculate statistical parameters, or determine cardiac trends and determine if the patient's heart 102 (shown in FIG. 1) is exhibiting myocardial instability or another physiological condition. Once the user workstation 1010 has finished performing its calculations, the user workstation 1010 may either download the results to the cell phone 1016, the PDA 1018, the local RF transceiver 1008, the programmer 1006, or to the server 1002 to be stored on the database 1004.

Figure 11:
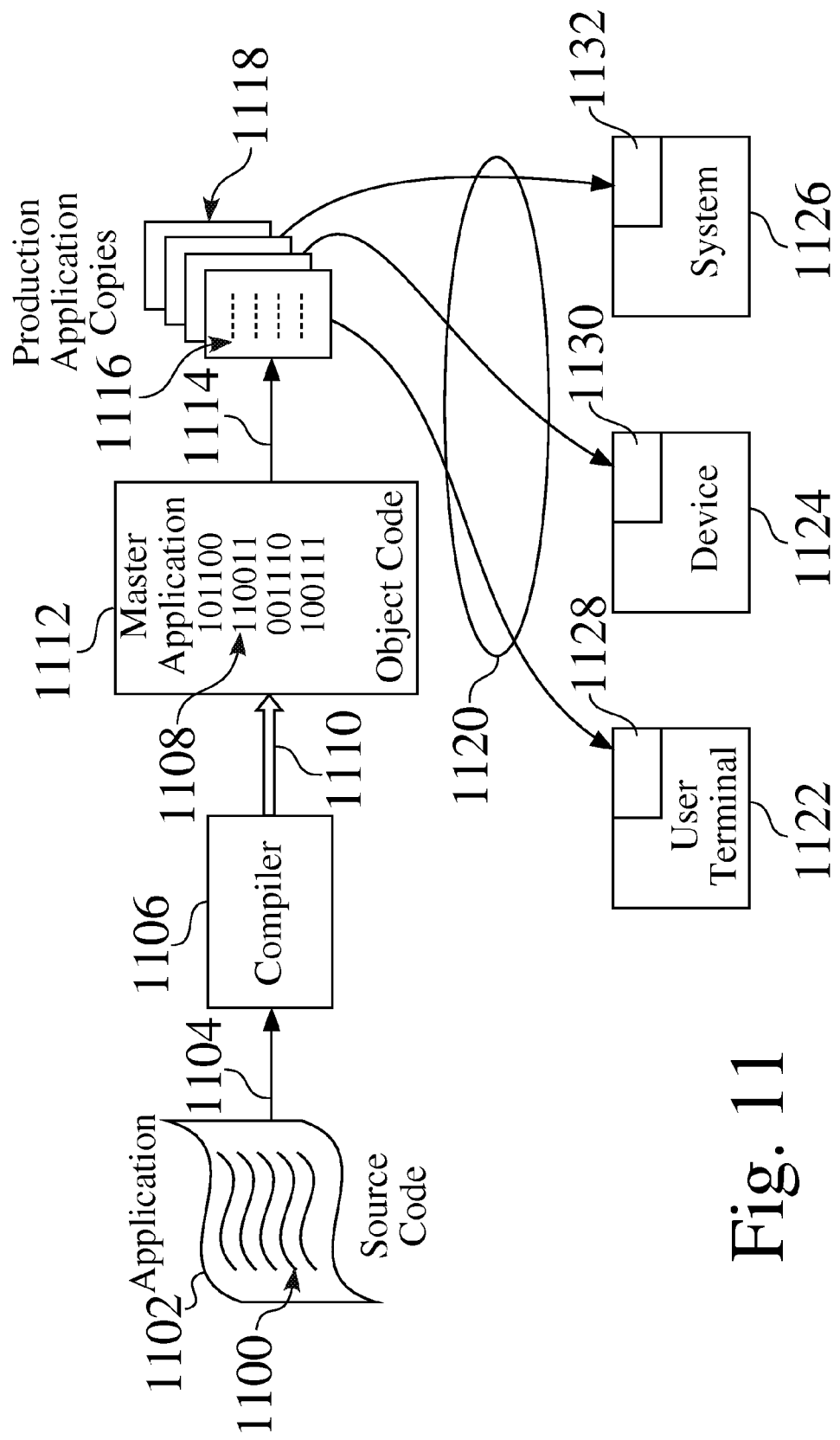
FIG. 11 illustrates a block diagram of exemplary manners in which embodiments of the present invention may be stored, distributed and installed on a computer-readable medium.

FIG. 11 illustrates a block diagram of exemplary manners in which embodiments of the present invention may be stored, distributed and installed on a computer-readable medium. In FIG. 11, the "application" represents one or more of the methods and process operations discussed above. For example, the application may represent the process carried out in connection with FIGS. 1 through 10 as discussed above. As shown in FIG. 11, the application is initially generated and stored as source code 1100 on a source computer-readable medium 1102. The source code 1100 is then conveyed over path 1104 and processed by a compiler 1106 to produce object code 1108. The object code 1108 is conveyed over path 1110 and saved as one or more application masters on a master computer-readable medium 1112. The object code 1108 is then copied numerous times, as denoted by path 1114, to produce production application copies 1116 that are saved on separate production computer-readable medium 1118. The production computer-readable medium 1118 is then conveyed, as denoted by path 1120, to various systems, devices, terminals and the like. In the example of FIG. 11, a user terminal 1122, a device 1124 and a system 1126 are shown as examples of hardware components, on which the production computer-readable medium 1118 are installed as applications (as denoted by 1128 through 1132). For example, the production computer-readable medium 1118 may be installed on the IMD 100 (shown in FIG. 1) and/or the microcontroller 800 (shown in FIG. 8).

The source code may be written as scripts, or in any high-level or low-level language. Examples of the source, master, and production computer-readable medium 1102, 1112 and 1118 include, but are not limited to, CDROM, RAM, ROM, Flash memory, RAID drives, memory on a computer system and the like. Examples of the paths 1104, 1110, 1114, and 1120 include, but are not limited to, network paths, the internet, Bluetooth, GSM, infrared wireless LANs, HIPERLAN, 3G, satellite, and the like. The paths 1104, 1110, 1114, and 1120 may also represent public or private carrier services that transport one or more physical copies of the source, master, or production computer-readable medium 1102, 1112 or 1118 between two geographic locations. The paths 1104, 1110, 1114 and 1120 may represent threads carried out by one or more processors in parallel. For example, one computer may hold the source code 1100, compiler 1106 and object code 1108. Multiple computers may operate in parallel to produce the production application copies 1116. The paths 1104, 1110, 1114, and 1120 may be intra-state, inter-state, intra-country, inter-country, intra-continental, inter-continental and the like.

The operations noted in FIG. 11 may be performed in a widely distributed manner world-wide with only a portion thereof being performed in the United States. For example, the application source code 1100 may be written in the United States and saved on a source computer-readable medium 1102 in the United States, but transported to another country (corresponding to path 1104) before compiling, copying and installation. Alternatively, the application source code 1100 may be written in or outside of the United States, compiled at a compiler 1106 located in the United States and saved on a master computer-readable medium 1112 in the United States, but the object code 1108 transported to another country (corresponding to path 1114) before copying and installation. Alternatively, the application source code 1100 and object code 1108 may be produced in or outside of the United States, but production application copies 1116 produced in or conveyed to the United States (for example, as part of a staging operation) before the production application copies 1116 are installed on user terminals 1122, devices 1124, and/or systems 1126 located in or outside the United States as applications 1128 through 1132.

As used throughout the specification and claims, the phrases "computer-readable medium" and "instructions configured to" shall refer to any one or all of (i) the source computer-readable medium 1102 and source code 1100, (ii) the master computer-readable medium and object code 1108, (iii) the production computer-readable medium 1118 and production application copies 1116 and/or (iv) the applications 1128 through 1132 saved in memory in the terminal 1122, device 1124 and system 1126.

In accordance with certain embodiments, methods and systems are provided that are able to analyze physiological parameters in order to monitor myocardial instability. Embodiments described herein permit the monitoring of patterns of heartbeat-to-heartbeat variations in physiological parameters. The monitoring of patterns in the physiological parameters may aid physicians in identifying risk of tachyarrhythmia and sudden cardiac death and in detecting and tracking the progression of cardiac disease, for example.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer readable storage medium for a computing device having a memory and a microcontroller, the non-transitory computer readable storage medium comprising instructions to:
   direct the memory to store a physiological parameter representative of myocardial behavior over a set of cardiac cycles; and
   direct the microcontroller to:
      count a number of reversal points in values of the physiological parameter over the set of cardiac cycles; and
   identify myocardial instability based on the number of reversal points in the values of the physiological parameter counted over the set of cardiac cycles, wherein the instructions direct the microcontroller to determine first and last reversal points in the set of cardiac cycles and calculate a reversal point percentage based on a relation of the number of the reversal points counted and a number of heartbeats between the first and last reversal points.

2. The non-transitory computer readable storage medium of claim 1, wherein the instructions direct the microcontroller to initiate a responsive action when myocardial instability is identified.

3. The non-transitory computer readable storage medium of claim 1, wherein each of the reversal points corresponds to a value of the physiological parameter, during a current cardiac cycle, that exceeds values of the physiological parameter during a prior and a subsequent cardiac cycle.

4. The non-transitory computer readable storage medium of claim 1, wherein each of the reversal points corresponds to a value of the physiological parameter, during a current cardiac cycle, that is less than values of the physiological parameter during a prior and a subsequent cardiac cycle.

5. The non-transitory computer readable storage medium of claim 1, wherein the instructions direct the microcontroller to calculate differences between values of the physiological parameter for consecutive cardiac cycles and detect the reversal points when a current difference exceeds differences for prior and subsequent cardiac cycles.

6. The non-transitory computer readable storage medium of claim 1, wherein the instructions direct the microcontroller to calculate differences between values of the physiological parameter for consecutive cardiac cycles and detect the reversal points when a current difference is less than differences for prior and subsequent cardiac cycles.

7. The non-transitory computer readable storage medium of claim 1, wherein the physiologic parameters represent at least one of a Q-T interval, QRS amplitude, P-wave amplitude, T-wave amplitude and R-R interval.

8. A non-transitory computer readable storage medium for a computing device having a memory and a microcontroller, the non-transitory computer readable storage medium comprising instructions to:
   direct the memory to store a physiological parameter representative of myocardial behavior over a set of cardiac cycles; and
   direct the microcontroller to:
      count a number of reversal points in values of the physiological parameter over the set of cardiac cycles; and
      identify myocardial instability based on the number of reversal points in the values of the physiological parameter counted over the set of cardiac cycles, wherein the instructions direct the microcontroller to calculate a reversal point percentage based on the number of the reversal points counted in the set of cardiac cycles and identify myocardial instability if the reversal point percentage exceeds a predetermined threshold.

9. A non-transitory computer readable storage medium for a computing device having a memory and a microcontroller, the non-transitory computer readable storage medium comprising instructions to:
   direct the memory to store a physiological parameter representative of myocardial behavior over a set of cardiac cycles; and
   direct the microcontroller to:
      count a number of reversal points in values of the physiological parameter over the set of cardiac cycles; and
   identify myocardial instability based on the number of reversal points in the values of the physiological parameter counted over the set of cardiac cycles, wherein the instructions direct the microcontroller to calculate a reversal point percentage based on the number of the reversal points counted in the set of cardiac cycles; and direct the memory to save the reversal point percentages for multiple sets of cardiac cycles.

10. A non-transitory computer readable storage medium for a computing device having a memory and a microcontroller, the non-transitory computer readable storage medium comprising instructions to:
 direct the memory to store a physiological parameter representative of myocardial behavior over a set of cardiac cycles; and
 direct the microcontroller to:
  count a number of reversal points in values of the physiological parameter over the set of cardiac cycles; and
identify myocardial instability based on the number of reversal points in the values of the physiological parameter counted over the set of cardiac cycles, wherein the instructions direct the microcontroller to calculate a reversal point percentage for each of multiple sets of cardiac cycles, the reversal point percentage for each set of cardiac cycles based on the number of the reversal points counted in the set; and to determine a trend in the reversal point percentages.

11. A device for analyzing myocardial instability, the device comprising:
 a memory for storing physiological parameters obtained by an implantable medical device and representative of myocardial behavior over a set of cardiac cycles; and
 a microcontroller for counting a number of reversal points in values of the physiological parameter over the set of cardiac cycles and identifying myocardial instability based on the number of the reversal points in the values of the physiological parameter counted over the set of cardiac cycles, wherein the microcontroller determines first and last reversal points in the set of cardiac cycles and calculates a reversal point percentage based on a relation of the number of the reversal points counted and a number of heartbeats between the first and last reversal points.

12. A device for analyzing myocardial instability, the device comprising:
 a memory for storing physiological parameters obtained by an implantable medical device and representative of myocardial behavior over a set of cardiac cycles; and
 a microcontroller for determining reversal points in the physiological parameter over the set of cardiac cycles and identifying myocardial instability based on the reversal points in the physiological parameter, wherein the microcontroller calculates a reversal point percentage based on a number of the reversal points in the set of cardiac cycles; and the memory saves the reversal point percentages for multiple sets of cardiac cycles.

13. A device for analyzing myocardial instability, the device comprising:
 a memory for storing physiological parameters obtained by an implantable medical device and representative of myocardial behavior over a set of cardiac cycles; and
 a microcontroller for counting a number of reversal points in values of the physiological parameter over the set of cardiac cycles and identifying myocardial instability based on the number of the reversal points in the values of the physiological parameter counted over the set of cardiac cycles, wherein the microcontroller calculates a reversal point percentage for each of multiple sets of cardiac cycles and determines a trend in the reversal point percentages, the reversal point percentage for each set of cardiac cycles based on a number of the reversal points in the set.

14. The device of claim 13, wherein the physiologic parameters represent at least one of a Q-T interval, QRS amplitude, P-wave amplitude, T-wave amplitude and R-R interval.

15. The device of claim 13, wherein each of the reversal points corresponds to a value of the physiological parameter, during a current cardiac cycle, that exceeds values of the physiological parameter during a prior and a subsequent cardiac cycle.

16. The device of claim 13, wherein each of the reversal points corresponds to a value of the physiological parameter, during a current cardiac cycle, that is less than values of the physiological parameter during a prior and a subsequent cardiac cycle.

17. The device of claim 13, wherein the microcontroller calculates differences between values of the physiological parameter for consecutive cardiac cycles and detects the reversal points when a current difference exceeds differences for prior and subsequent cardiac cycles.

18. The device of claim 13, wherein the microcontroller calculates differences between values of the physiological parameter for consecutive cardiac cycles and detects the reversal points when a current difference is less than differences for prior and subsequent cardiac cycles.

19. The device of claim 13, wherein the microcontroller initiates a responsive action when myocardial instability is identified.

* * * * *